(12) United States Patent
Sharma et al.

(10) Patent No.: US 6,979,436 B2
(45) Date of Patent: Dec. 27, 2005

(54) OPIOID METALLOPEPTIDE COMPOSITIONS AND METHODS

(75) Inventors: Shubh D. Sharma, Cranbury, NJ (US); Wei Yang, Edison, NJ (US); Hui-Zhi Cai, East Brunswick, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 211 days.

(21) Appl. No.: 10/150,979

(22) Filed: May 17, 2002

(65) Prior Publication Data

US 2005/0181447 A1    Aug. 18, 2005

Related U.S. Application Data

(63) Continuation-in-part of application No. PCT/US00/31797, filed on Nov. 17, 2000.

(60) Provisional application No. 60/166,582, filed on Nov. 19, 1999.

(51) Int. Cl.$^7$ ........................ A61K 51/00; A61M 36/14
(52) U.S. Cl. ................... 424/1.69; 424/1.11; 424/1.65; 424/9.1; 534/14
(58) Field of Search ............................. 424/1.11, 1.65, 424/1.69; 534/7, 10–16; 530/300, 324–331, 530/317

(56) References Cited

U.S. PATENT DOCUMENTS

| | | | |
|---|---|---|---|
| 5,432,018 A | | 7/1995 | Dower et al. |
| 5,443,816 A | * | 8/1995 | Zamora et al. ............ 424/1.69 |
| 5,610,271 A | | 3/1997 | Dooley et al. |
| 5,663,295 A | | 9/1997 | Moreau et al. |
| 5,665,865 A | | 9/1997 | Lerner et al. |
| 5,668,254 A | | 9/1997 | Deghenghi |
| 5,679,548 A | | 10/1997 | Barbas et al. |
| 5,733,881 A | | 3/1998 | Schiller |
| 5,770,178 A | | 6/1998 | Itaya et al. |
| 5,811,400 A | | 9/1998 | Schiller |
| 5,872,097 A | | 2/1999 | Fholenhag et al. |
| 5,883,293 A | | 3/1999 | Gilon et al. |
| 5,885,958 A | | 3/1999 | Zadina et al. |
| 5,891,418 A | | 4/1999 | Sharma |
| 5,919,897 A | | 7/1999 | Dooley et al. |
| 5,965,701 A | | 10/1999 | Junien et al. |
| 6,027,711 A | * | 2/2000 | Sharma ..................... 424/1.69 |
| 6,028,063 A | | 2/2000 | Kruse et al. |
| 6,048,527 A | | 4/2000 | Granoff et al. |
| 6,057,357 A | | 5/2000 | Horwell et al. |
| 6,150,335 A | | 11/2000 | Schiller |
| 6,284,769 B1 | | 9/2001 | Dunn et al. |
| 6,331,285 B1 | * | 12/2001 | Sharma ..................... 424/1.69 |
| 6,337,319 B1 | | 1/2002 | Wang |
| 2001/0009899 A1 | | 7/2001 | Keri et al. |
| 2001/0041746 A1 | | 11/2001 | Kyle et al. |
| 2002/0012948 A1 | | 1/2002 | Sharma et al. |

FOREIGN PATENT DOCUMENTS

| | | |
|---|---|---|
| WO | WO 97/07130 | 2/1997 |
| WO | WO 98/56796 | 12/1998 |
| WO | WO 99/10016 | 3/1999 |
| WO | WO 99/59997 | 11/1999 |
| WO | WO 99/65932 | 12/1999 |
| WO | WO 00/08027 | 2/2000 |
| WO | WO 00/51539 | 9/2000 |

OTHER PUBLICATIONS

Pogozheva, Irina D., et al., "Opioid Receptor Three Dimensional Structures for distance Geometry Caluclations with Hydrogen Bonding Constraints," Biophysical Journal, vol. 75, Aug. 1998, pp. 612-634.

Hruby, V.J., et al., "Cyclic Enkephalin Analogues with Exceptional Potentcy and Selectivity for Opioid Receptors," ed. 40, J. Med. Chem. 1997, pp. 3957-3962.

Fabris, D., et al., "Investigation of Zinc Chelation in Zinc-Finger Arrays by Electrospray Mass Spectrometry", Inorganic Chemistry, vol. 38, (1999), 1322-1325.

Giblin, Michael F., et al., "Design and Characterization of 0-melanocortin Peptide Analogs Cyclized through Rhenium and Technetium Metal Coordination", Proceedings of National Academy Science USA, vol. 95, (Oct. 1998), 12814-12818.

Shi, Yi-Qun , et al., "Conformationally Constrained Metallpeptide Template for Melanocortin-1 Receptor", American Chemistry Society, 218th ACS National Meeting, Abstracts of Papers, Part 1, Abstract MEDI 257, (Aug. 22, 1999).

* cited by examiner

Primary Examiner—Dameron L. Jones
(74) Attorney, Agent, or Firm—Stephen A. Slusher

(57) ABSTRACT

Metallopeptides and metallopeptide combinatorial libraries specific for opioids receptors are provided, for use in biological, pharmaceutical and related applications. The metallopeptides and combinatorial libraries are made of peptides, peptidomimetics and peptide-like constructs, in which the peptide, peptidomimetic or construct is conformationally fixed in a biologically active configuration specific for one or more opioid receptors on complexation of a metal ion-binding portion thereof with a metal ion.

36 Claims, No Drawings

OPIOID METALLOPEPTIDE COMPOSITIONS AND METHODS

CROSS-REFERENCE TO RELATED APPLICATIONS

This is a continuation-in-part application of International Application PCT/US00/31797 filed under the Patent Cooperation Treaty, entitled Opioid Metallopeptide Compositions and Methods, with an international filing date of Nov. 17, 2000, and published in English under PCT Article 21(2) and now abandoned, and the specification thereof is incorporated herein by reference. This application claims the benefit of the filing of U.S. Provisional Patent Application Ser. No. 60/166,582, entitled Opioid Analgesic Metallopeptide Compositions and Methods, filed on Nov. 19, 1999, and the specification thereof is incorporated herein by reference.

This application is related to P.C.T. Patent Application Serial No. PCT/US99/29743, entitled Metallopeptide Combinatorial Libraries and Applications, filed 14 Dec. 1999; P.C.T. Patent Application Serial No. PCT/US00/16396, entitled Melanocortin Metallopeptide Constructs, Combinatorial Libraries and Applications, filed 14 Jun. 2000; U.S. Pat. No. 6,027,711, entitled Structurally Determined Metallo-Constructs and Applications, issued Feb. 22, 2000; and U.S. Pat. No. 5,891,418, entitled Peptide–Metal Ion Pharmaceutical Constructs and Applications, issued Apr. 6, 1999; the teachings of all of which are incorporated herein by reference as if set forth in full.

GOVERNMENT RIGHTS

The U.S. Government has a paid-up license in this invention and the right in limited circumstances to require the patent owner to license others on reasonable terms as provided for by the terms of Grant No. $R_{43}$ DA13058-01 awarded by the National Institute on Drug Abuse of the National Institutes of Health of the U.S. Department of Health and Human Services.

BACKGROUND OF THE INVENTION

1. Field of the Invention (Technical Field):

The present invention relates to metallopeptides, and metallopeptide combinatorial libraries specific for opioid receptors, and which are agonist, antagonist or mixed agonist-antagonists, including methods for the use and making of the same.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Opioid Receptors and Use of Opioids in Medicine. Morphine, related narcotics and other synthetic non-peptide opioids have been used through all of recorded history to alleviate pain. However, persistent use of these opiates in pain management is associated with several serious drawbacks such as addiction, depression of cardiovascular and respiratory functions and acute constipation. Recent strides in opiate research have established that most of these ill effects of narcotics are mediated through the mu ($\mu$) opioid receptors. The delta ($\delta$)-receptor, on the other hand, mediates antinociception without these serious side effects. (See, for example, Dhawan B N, Cesselin F, Raghubir R, Reisine T, Bradley P B, Portoghese P S, Hamon M. International union of pharmacology XII. Classification of opioid receptors. *Pharmacol. Rev.* 48: 567–592, 1996; Fundytus M E, Schiller P W, Shipiro M et al. Attenuation of morphine tolerance and dependence with highly selective delta opioid receptor antagonist TIPP. *Eur J Pharmacol* 286:105–108, 1995; Jiang Q, Mosberg H I, Porreca F. Selective modulation of morphine antinociception, but not development of tolerance, by delta receptor agonist. *Eur J Pharmacol* 186:137–141, 1990). Major research effort in past several years has been focused on developing potent and selective $\delta$ receptor agonists for clinical use in pain management. See, for example, U.S. Pat. No. 5,872,097.

The $\mu$-, $\delta$-, and kappa ($\kappa$) opiate receptors are all G protein-coupled, 7-transmembrane receptors. All these receptors can bind various peptide analogs containing a common opiate pharmacophore, Tyr-$[X]_n$-Phe (message sequence). All the endogenous and naturally occurring opioid peptides (such as enkephalins, endorphins, dynorphins, casomorphins, deltorphins and dermorphin) display this pharmacophore. Excellent progress has been made in developing a variety of potent and receptor-selective opioid peptide analogs (See, for example, Schiller P W, Weltrowska G, et al. Subtleties of structure-agonist versus antagonist relationships of opioid peptides and peptidomimetics. *J Recept Signal Transduct Res* 19:573–88, 1999; Hruby V J, Bartosz-Bechowski H, Davis P et al. Cyclic enkephalin analogues with exceptional potency and selectivity for delta-opioid receptors. *J Med Chem* 40:3957–62, 1997), peptidomimetics and non-peptide molecules (See, for example, Liao S, Alfaro-Lopaz J, Shederovich M D, et al. De novo design, synthesis and biological activity of high affinity and selective non-peptide agonist of the delta-opioid receptors. *J Med Chem* 41:4767–4776, 1998; Gao P, Larson D L, Portoghese. Synthesis of 7-arylmorphinans. Probing the address requirements for selectivity at opioid delta receptors. *J Med Chem* 41:3091–3098, 1998). Several of these ligands are highly selective and potent for the $\delta$ opiate receptor and produce antinociception under strict experimental conditions.

Besides potency and receptor selectivity, there are two other requisites for a clinically useable opiate receptor-based analgesic for pain management. The drug must be able to cross the blood-brain-barrier (BBB) to reach and interact with its brain receptor, and it must be orally active. Most prior art peptide analogs and peptidomimetics are not systemically bioavailable, either in terms of crossing the BBB or oral absorption, which has precluded their further clinical development as analgesics. Many non-peptide $\delta$ ligands are systemically active in producing analgesia, and thus capable of crossing the BBB, but are not active upon oral administration. There is a clear need for potent and selective $\delta$ opiate receptor agonists that are orally active in producing antinociception. In general, there is a need for selective opiate receptor agonists and antagonists to the $\mu$-, $\delta$, and $\kappa$-opiate receptors.

In general, prior research has been conducted on both peptide and non-peptide opioids. For example, U.S. Pat. No. 5,965,701 discloses receptor-specific peptides, while U.S. Pat. Nos. 6,028,063 and 6,057,357 disclose non-peptide $\kappa$ opioid agonists and PCT/US99/18021 discloses a $\kappa$ receptor antagonist. U.S. Pat. Nos. 5,885,958 and 5,919,897 and PCT/US99/13638 disclose $\mu$-opioid receptor-specific agents which are peptides, peptidomimetics or other small molecules, displaying both agonist and antagonist activity.

Peptide Libraries and Combinatorial Chemistry. U.S. Pat. No. 6,027,711 and PCT/US00/16396 teach combinatorial chemistry techniques, including a summary of methods employed as tools for rapid drug discovery. A library of peptides and other small molecules, with its enormous pool of structurally diverse molecules, is well suited for both lead generation as well as lead optimization. Libraries of a variety of molecular species have been described in literature and screened for drug discovery. These molecular species include peptides, peptoids, peptidomimetics, oligonucleotides, benzodiazepines, and other libraries of small organic molecules.

Various approaches used to construct a library of structurally diverse chemical compounds include chemical synthesis and genetic engineering methods. Chemically synthesized libraries can be either soluble (a mixture of various compounds in a solution) or solid (compounds synthesized on a solid surface). Libraries produced by genetic engineering tools are largely composed of peptide molecules, and are similar to solid-phase libraries in the sense that the peptide sequences are displayed or attached on the surface of plasmids, bacteriophages or bacteria used for their production.

SUMMARY OF THE INVENTION
(DISCLOSURE OF THE INVENTION)

In one preferred embodiment the invention provides a construct including a metal ion-binding domain made up of two or more linked amino acid residues forming a nitrogen-containing and sulfur-containing ligand available for complexing with a metal ion, wherein the construct is conformationally constrained in a structure specific for one or more opioid receptors, preferably including a phenol moiety and a phenyl moiety, upon complexing the metal ion-binding domain with a metal ion.

In another preferred embodiment, the invention provides a manufactured peptide and pharmaceutically acceptable salts thereof including a metal ion-binding domain that is made up of two or more contiguous amino acids and a determined biological-function domain specific for one or more opioid receptors, wherein at least a portion of the biological-function domain is co-extensive with at least a portion of the metal ion-binding domain, and wherein the biological-function domain is conformationally constrained and includes a phenol moiety and a phenyl moiety upon complexing the metal ion-binding domain with a metal ion.

The invention thus includes peptide compositions and pharmaceutical salts thereof of the formulas: $R_1$—$R_2$—$R_3$—$R_4$, $R_5$—$R_2$—$R_6$—$R_3$—$R_7$, $R_5$—$R_8$—$R_2$—$R_6$—$R_3$—$R_7$, $R_9$—$R_1$—$R_3$—$R_{10}$, $R_5$—$R_{11}$—$R_6$—$R_{12}$, $R_5$—$R_{11}$—$R_{13}$—$R_3$—$R_{10}$, and $R_{14}$—$R_6$—$R_{15}$—$R_3$—$R_{16}$, wherein $R_1$ is an L- or D-amino acid with a phenol moiety side chain, and with an —N available for complexation to a metal ion;

$R_2$ is a neutral or basic L- or D-amino acid with an —N available for complexation to a metal ion;

$R_3$ is L- or D-Cys, L- or D-homoCys, L- or D-Pen or a derivative or homolog of any of the foregoing, with both an —N and —SH available for complexation to a metal ion;

$R_4$ is an L- or D-amino acid with a neutral aromatic side chain or side chain with an aromatic ring substituted halogen, nitro or alkyl group, or is a des-carboxyl derivative corresponding to such L- or D-amino acid;

$R_5$ is an L- or D-amino acid with a phenol moiety side chain, excluding des-carboxy derivatives;

$R_6$ is an L- or D-amino acid with a neutral side chain or side chain with an aromatic ring substituted halogen, nitro or alkyl group, with an —N available for complexation to a metal ion;

$R_7$ is a free carboxylate or terminal amide of $R_3$ or a neutral or basic L- or D-amino acid, or is a des-carboxyl derivative corresponding to such L- or D-amino acid;

$R_8$ is a neutral or basic L- or D-alpha or -omega amino acid, or is a derivative corresponding to such, including higher omega amino aliphatic carboxylic acid homologs and cysteine;

$R_9$ is an L- or D-amino acid with a basic functional group side chain, and with an —N available for complexation to a metal ion;

$R_{10}$ is a free carboxylate, primary amide or aryl or aralkyl chain substituted amide of $R_3$, or an L- or D-amino acid with a neutral aromatic side chain or side chain with a ring substituted halogen, nitro or alkyl group;

$R_{11}$ is L- or D-Cys, L- or D-homoCys, L- or D-Pen or a derivative or homolog of any of the foregoing, with an —SH available for complexation to a metal ion;

$R_{12}$ is a neutral L- or D-amino acid with an —N available for complexation to a metal ion, and with a terminal amide with an —N available for complexation to a metal ion;

$R_{13}$ is an L- or D-amino acid with a neutral aliphatic or aromatic side chain or side chain with a ring substituted halogen, nitro or alkyl group, with an —N available for complexation to a metal ion;

$R_{14}$ is a neutral or basic L- or D-alpha or -omega amino acid, or is a derivative corresponding to such, excluding higher omega amino aliphatic carboxylic acid homologs;

$R_{15}$ is a L- or D-amino acid with an —N available for complexation to a metal ion and hydrogen bond forming groups in the side chain;

$R_{16}$ an L- or D-amino acid with a phenol moiety side chain, including des-carboxy derivatives.

In each of the foregoing compositions, the composition may be complexed with a metal ion, including rhenium, through the provided residues or amino acids with —N or —SH available for complexation to a metal ion. The compositions are characterized in that the compositions are substantially more specific for one or more opioid receptors when complexed with a metal ion than is the same composition when not complexed with a metal ion. The compositions may be an agonist, an antagonist or a mixed agonist/antagonist for one or more opioid receptors, including $\mu$-, $\delta$-, and $\kappa$-opiate receptors.

In another preferred embodiment, the invention provides a combinatorial library targeted to opioid receptors of different sequence peptide members synthesized on solid phase, where each constituent library member comprises:

(a) a peptide sequence of three or more amino acid residues bound to solid phase characterized by (i) a sequence of two or more amino acid residues forming a metal ion-binding domain and including at least one amino acid residue containing at least one S wherein the said S is protected by an orthogonal S-protecting group, (ii) a sequence of one or more amino acid residues at the N- or C-terminus of the metal ion-binding domain, or at both the N- and C-terminus of the metal ion-binding domain, and (iii) a cleavable bond attaching the peptide sequence to solid phase; and (b) a unique selection or sequence of amino acid residues in the peptide sequence of at least one of the constituent members of the library;

wherein the orthogonal S-protecting group may be removed without cleaving the peptide sequence from the solid phase.

The invention further provides a combinatorial library targeted to opioid receptors of different sequence peptidomimetic members synthesized on solid phase, where each constituent library member comprises:

(a) a peptidomimetic sequence of a combination of three or more amino acid residues and mimics of amino acid residues bound to solid phase characterized by (i) a sequence of two or more amino acid residues, mimics of amino acid residues or combinations thereof forming a metal ion-binding domain and including at least one amino acid residue or mimic of an amino acid residue containing at least one S wherein the said S is protected by an orthogonal S-protecting group, (ii) a sequence of one or more amino acid residues, mimics of amino acid residues or combinations thereof at the N- or C-terminus of the metal ion-binding domain, or at both the N- and C-terminus of the metal ion-binding domain, and (iii) a cleavable bond attaching the peptidomimetic sequence to solid phase; and (b) a unique selection or sequence of amino acid residues, mimics of amino acid residues or combinations thereof in the peptidomimetic sequence of at least one of the constituent members of the library;

wherein the orthogonal S-protecting group may be removed without cleaving the peptidomimetic sequence from the solid phase.

The invention further provides a combinatorial library targeted to opioid receptors of different sequence peptide or peptidomimetic members synthesized in solution, where each constituent library member comprises:

(a) a peptidomimetic sequence of a combination of three or more amino acid residues and mimics of amino acid residues bound to solid phase characterized by (i) a sequence of two or more amino acid residues, mimics of amino acid residues or combinations thereof forming a metal ion-binding domain and including at least one amino acid residue or mimic of an amino acid residue containing at least one S wherein the said S is protected by an S-protecting group, which may be orthogonal or non-orthogonal, (ii) a sequence of one or more amino acid residues, mimics of amino acid residues or combinations thereof at the N- or C-terminus of the metal ion-binding domain, or at both the N- and C-terminus of the metal ion-binding domain; and (b) a unique selection or sequence of amino acid residues, mimics of amino acid residues or combinations thereof in the peptidomimetic sequence of at least one of the constituent members of the library.

In a preferred embodiment, in each of the combinatorial libraries provided each constituent member includes an amino acid residue or mimic thereof with a phenol moiety, and an amino acid residue or mimic thereof with a phenyl moiety. The constituent members may be so constructed such that both amino acid residues or mimics thereof with a phenol moiety and phenyl moiety are part of the metal ion-binding domain, or alternatively may be constructed such that at most only one of the amino acid residues or mimics thereof with either a phenol moiety or phenyl moiety are part of the metal ion-binding domain.

In each of the combinatorial libraries, the metal ion-binding domain may include at least one N available for binding to a metal ion upon removal of the orthogonal S-protecting group, and preferably comprises three residues forming an $N_3S_1$ ligand. In the combinatorial libraries wherein an orthogonal S-protecting group is employed, such orthogonal S-protecting group can be S-thio-butyl, acetamidomethyl, 4-methoxytrityl, S-sulfonate or 3-nitro-2-pyridinesulfenyl. Preferably the orthogonal S-protecting group may be removed from constituent library members thereof without otherwise altering the constituent library members or any amino acid side chain protecting group therein. Structural diversity in the combinatorial libraries may occur in the metal ion-binding domain or alternatively may occur outside the metal ion-binding domain. In one embodiment, each member of the combinatorial libraries includes a phenol moiety and a phenyl moiety.

For peptide combinatorial libraries, the at least one amino acid residue containing at least one S wherein the said S is protected by an orthogonal S-protecting group can be any L- or D-3mercapto amino acid, including but not limited to L- or D-cysteine or L- or D-penicillamine. For peptidomimetic combinatorial libraries, the at least one amino acid residue or mimic of an amino acid residue containing at least one S wherein the said S is protected by an orthogonal S-protecting group can be any L- or D-3-mercapto amino acid, including but not limited to L- or D-cysteine or L- or D-penicillamine; 3-mercapto phenylananine; 2-mercaptoacetic acid; 3-mercaptopropionic acid; 2mercaptopropionic acid; 3-mercapto-3,3,-dimethyl propionic acid; 3-mercapto-3,3,-diethyl proprionic acid; 3-mercapto,3-methyl propionic acid; 2-mercapto,2-methyl acetic acid; 3-cyclopentamethylene,3mercaptopropionic acid; or 2-cyclopentamethylene,2-mercaptoacetic acid.

It is an object of this invention to devise, demonstrate and illustrate the preparation and use of highly specific conformationally restricted peptides, including peptoids, related pseudopeptides, and peptidomimetics, formed by complexing sequences thereof to a desired metal ion so that the topography of the side chains in the resulting complex is a biologically active three-dimensional structure specific for opioid receptors.

Another object of this invention is to provide peptide-metal ion complexes specific for opioid receptors which have a higher level of stability and are less susceptible to proteolysis than either the uncomplexed peptide or other peptides known in the art.

Another object of this invention is to provide peptide-metal ion complexes which are specific for different subsets of opioid receptors, such as specific only for δ opioid receptors and not for µ or other opioid receptors.

Another object of this invention is to provide peptide-metal ion complexes which are specific for δ opioid receptors and which are agonists.

Another object of this invention is to provide peptide-metal ion complexes that are specific for one of µ-, δ-, or κ-opiate receptors, and which are agonists, antagonists, or mixed agonists and antagonists.

Another object of this invention is to provide for peptide analogs which are not conformationally restricted in the absence of a metal ion, whereby the uncomplexed peptide analog is either inactive or demonstrates low to moderate potency, but which are conformationally restricted on complexation with a metal ion and thereupon specific for opioid receptors with a higher potency.

Another object of this invention is to utilize metal complexation in a peptide specific for opioid receptors to cause specific regional conformational restrictions in the peptide so that the peptide conformation at the metal binding site is conformationally fixed on metal complexation.

Another object of this invention is to provide a metallopeptide construct specific for one or more opioid receptors, wherein the metallopeptide construct includes a residue or mimic thereof with a phenol moiety and a residue or mimic thereof with a phenyl moiety.

Another object of this invention is to provide a class of metallopeptide constructs specific for one or more opioid receptors, wherein each metallopeptide construct includes residues or mimics thereof with a phenyl moiety and separately with a phenyl moiety, with the residues or mimics with phenol and phenyl moieties either within or without the sequence of residues or mimics involved in complexation of the metal ion.

Another object of this invention is to complex a peptide to a metal ion, whereby the resulting metallopeptide is specific for opioid receptors, and exhibits a preferred in vivo biodistribution profile, rate and mode of clearance, bioavailability and pharmacokinetics in mammals.

Another object of this invention is to provide peptide-metal ion complexes specific for opioid receptors utilizing stable non-radioactive metal ions, for use in pain management.

Another object of this invention is to provide peptide-metal ion complexes specific for opioid receptors which can transit the blood-brain barrier, and which may be administered by systemic means, including but not limited to intravenous administration and oral administration.

Another object of this invention is to provide peptide-metal ion complexes specific for opioid receptors which can transit the gut-blood barrier, without significant enzymatic or peptidase degradation, and may be adapted for oral administration.

Another object of this invention is to provide libraries of conformationally constrained peptide-metal ion complexes directed to opioid receptors.

Another object of this invention is to provide combinatorial peptide libraries of peptide-metal ion complexes specific for opioid receptors, wherein the peptides include a metal ion-binding domain, such that a specific conformational restriction is obtained upon complexing each peptide with a metal ion.

Another object of this invention is to provide combinatorial peptide libraries of peptide-metal ion complexes specific for opioid receptors, wherein the amino acids comprising the peptides may be naturally occurring amino acids, isomers and modifications of such amino acids, non-protein amino acids, post-translationally modified amino acids, enzymatically modified amino acids, constructs or structures designed to mimic amino acids, and the like, so that the library includes pseudopeptides and peptidomimetics.

Another object of this invention is to provide metallopeptide libraries specific for one or more specified opioid receptors, wherein the metallopeptides include a metal ion-binding domain, such that a determined conformational restriction is obtained upon complexing the peptides with a metal ion, and the metallopeptides further include distinct, unique and different amino acid sequences.

Another object of this invention is to provide both soluble or solid phase metallopeptide libraries specific for one or more specified opioid receptors, wherein the metallopeptides include a metal ion-binding domain.

Another object of this invention is to provide methods for synthesis of peptides specific for opioid receptors wherein the peptide contains one or more reactive —SH groups forming a part of a metal ion-binding domain, whereby the reactive —SH group or groups are protected during synthesis, and are deprotected only upon complexing the peptides with a metal ion.

Another object of this invention to provide libraries of conformationally constrained peptide-metal ion complexes as surrogates for reverse turn structures, such as beta turns and gamma turns commonly found in naturally occurring peptides and proteins specific for opioid receptors. The turns formed as a consequence of metal ion complexation are more stable than the naturally occurring turn structures, which are stabilized only by weaker interactions such as van der Waals' interactions and hydrogen bonds.

Another object of this invention is to provide combinatorial metallopeptide libraries specific for opioid receptors wherein each of the peptides forming the library contain a reverse turn structure as a consequence of metal ion complexation.

Another object of this invention is to provide a method for rapid and efficient complexation of a pool of diverse peptides specific for opioid receptors with a metal ion, including a rhenium metal ion.

Other objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the appended claims.

DESCRIPTION OF THE PREFERRED EMBODIMENTS (BEST MODES FOR CARRYING OUT THE INVENTION)

Definitions. Certain terms as used throughout the specification and claims are defined as follows:

The terms "bind," "binding," "complex," and "complexing," as used throughout the specification and claims, are generally intended to cover all types of physical and chemical binding, reactions, complexing, attraction, chelating and the like.

The "peptides" of this invention can be a) naturally-occurring, b) produced by chemical synthesis, c) produced by recombinant DNA technology, d) produced by biochemical or enzymatic fragmentation of larger molecules, e) produced by methods resulting from a combination of methods a through d listed above, or 0 produced by any other means for producing peptides.

By employing chemical synthesis, a preferred means of production, it is possible to introduce various amino acids which do not naturally occur along the chain, modify the N- or C-terminus, and the like, thereby providing for improved stability and formulation, resistance to protease degradation, and the like.

The term "peptide" as used throughout the specification and claims is intended to include any structure comprised of two or more amino acids, including chemical modifications and derivatives of amino acids. For the most part, the peptides of this invention comprise fewer than 100 amino acids, and preferably fewer than 60 amino acids, and most preferably ranging from about 2 to 20 amino acids. The amino acids forming all or a part of a peptide may be naturally occurring amino acids, isomers and modifications of such amino acids, non-protein amino acids, post-translationally modified amino acids, enzymatically modified amino acids, constructs or structures designed to mimic amino acids, and the like, so that the term "peptide" includes pseudopeptides and peptidomimetics, including structures which have a non-peptidic backbone. The term "peptide" also includes dimers or multimers of peptides. A "manufactured" peptide includes a peptide produced by chemical synthesis, recombinant DNA technology, biochemical or enzymatic fragmentation of larger molecules, combinations of the foregoing or, in general, made by any other method.

The "amino acids" used in this invention, and the term as used in the specification and claims, include the known naturally occurring protein amino acids, which are referred to by both their common three letter abbreviation and single letter abbreviation. See generally *Synthetic Peptides: A User's Guide*, G. A. Grant, editor, W.H. Freeman & Co., New York, 1992, the teachings of which are incorporated herein by reference, including the text and table set forth at pages 11 through 24. As set forth above, the term "amino acid" also includes isomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, cited above; Hruby V J, Al-obeidi F and Kazmierski W. Emerging approaches in the molecular design of receptor-selective peptide ligands; conformational, topographical and dynamic consideration. Biochem J 268:249–262, 1990; and Toniolo C. Conformationally restricted peptides through short-range cyclization. *Int J Peptide Protein Res* 35:287–300, 1990; the teachings of all of which are incorporated herein by reference. In addition, the following abbreviations have the meanings giving:

| | |
|---|---|
| Abu | gamma-amino butyric acid |
| Bip | biphenylalanine |
| Bz | Benzoyl |
| Dip | 3,3-Diphenylalanine |
| Et- | Ethyl |
| HPhe | Homophenylalanine |
| Nal | 3-(1-naphthyl)alanine |
| Phg | Phenylglycine |
| TFA | trifluoroacetyl |

A single amino acid, including stereoisomers and modifications of naturally occurring protein amino acids, non-protein amino acids, post-translationally modified amino acids, enzymatically synthesized amino acids, derivatized amino acids, constructs or structures designed to mimic amino acids, and the like, is sometimes referred to herein as a "residue."

The peptide and library constructs of this invention also include a metal ion, which may be an ionic form of any element in metallic form, including but not limited to metals and metalloids. The metal ion may, but need not, be radioactive, paramagnetic or superparamagnetic. The metal ion can be of any oxidation state of any metal, including oxidation states of vanadium (V), manganese (Mn), iron (Fe), cobalt (Co), nickel (Ni), copper (Cu), zinc (Zn), gallium (Ga), arsenic (As), selenium (Se), yttrium (Y), molybdenum (Mo), technetium (Tc), ruthenium (Ru), rhodium (Rh), palladium (Pd), silver (Ag), cadmium (Cd), indium (In), tin (Sn), tungsten (W), rhenium (Re), osmium (Os), iridium (Ir), platinum (Pt), gold (Au), mercury (Hg), thallium (Tl), lead (Pb), bismuth (Bi), polonium (Po), astatine (At), samarium (Sm), europium (Eu), and gadolinium (Gd). The metal ion can also be a radionuclide of any of the foregoing, including In, Au, Ag, Hg, Tc, Re, Sn, At, Y and Cu. A preferred metal ion with a tetradentate coordination sphere is Re. For radiopharmaceutical applications, or applications wherein a radioisotope is desirable for screening, an alpha-, gamma- or beta-emitting radionuclide may be employed.

The coordination sphere of various common metal ions, in general, is tetradentate to hexadentate. In one embodiment according to this invention, an amino acid or amino acid mimetic sequence is included within each library member such that it contains the desired number of groups (4 to 6 in most cases) for complexing with the metal ion. The molecule is designed so that, upon complexing with a metal ion, it forms a mimic of a reverse turn structure about the site of metal ion complexation. A metal with coordination number 4, 5 or 6, and complexing respectively with an amino acid sequence forming a tetra, penta, or hexadentate ligand, will fold and constrain the ligand. A highly flexible molecule like a peptide, in other words, is folded to form a kind of reverse turn upon its complexation with a metal. This resulting turn is a highly constrained structure in the conformational sense.

The biological-function domain of the peptide is a sequence of one or more amino acids which constitute a biologically active peptide sequence, exhibiting binding to a biological receptor found on cells, tissues, organs and other biological materials, including specifically an opioid receptor, thereby constituting the peptide as a member of a specific binding pair, and specifically including a biologically active peptide sequence that binds to one or more opioid receptors. The biological-function domain also includes any sequence, which may be consecutive amino acids (sychnological) or may be non-consecutive amino acids (rhegnylogical), of one or more amino acids which forms a ligand, which ligand is capable of forming a specific interaction with an acceptor or receptor found on neuronal and other cells in peripheral central tissue. The term "receptor" is intended to include both acceptors and receptors. The receptor may be a biological receptor. The sequence or biological-binding domain may transmit a signal to the cells, tissues or other materials associated with the biological receptor after binding, but such is not required. The metal-complexed peptide, and thus the biological-function domain, may be either an agonist or antagonist, or a mixed agonist-antagonist. A peptide or peptidomimetic complexed to a metal ion may further constitute a member of a "specific binding pair," which specific binding pair is made up of at least two different molecules, where one molecule has an area on the surface or in a cavity which specifically binds to a particular spatial and polar organization of the other molecule. Frequently, the members of a specific binding pair are referred to as ligand and receptor or anti-ligand.

The biological-function domain is further defined to include the portion of a construct, wherein the construct is a peptidomimetic, peptide-like, or metallo-construct molecule, which upon binding of the construct with a metal ion, is biologically active, exhibiting binding to a opioid receptor found on cells, tissues, organs and other biological materials. The biological-function domain may, in this instance, be sychnological or rhegnylogical, and generally has the attributes and functions of a biological-function domain of a peptide. The biological-function domain may be coextensive with all or a portion of the residues complexing the metal ion, so that the same amino acid sequence or other residues which constitute the biological-function domain also constitute all or a part of the amino acid sequence or other residues complexed to the metal ion. In some instances, one or more amino acids complexing the metal ion will form a part of the biological-function domain, and one or more additional amino acids, which are not complexed to the metal ion, form the remainder of the biological-function domain.

Conformational constraint refers to the stability and preferred conformation of the three-dimensional shape assumed by a peptide or other construct. Conformational constraints include local constraints, involving restricting the conformational mobility of a single residue in a peptide; regional constraints, involving restricting the conformational mobility of a group of residues, which residues may form some secondary structural unit; and global constraints, involving the entire peptide structure. See generally *Synthetic Peptides: A User's Guide*, cited above.

The primary structure of a peptide is its amino acid sequence. The secondary structure deals with the conformation of the peptide backbone and the folding up of the segments of the peptide into regular structures such as α-helices, β-sheets, turns and the like. Thus, the three-dimensional shape assumed by a peptide is directly related to its secondary structure. See generally *Synthetic Peptides: A User's Guide*, cited above, including the text, figures and tables set forth at pages 24–33, 39–41 and 58–67. A global structure refers to a peptide structure that exhibits a preference for adopting a conformationally constrained three-dimensional shape.

The product resulting from the methods set forth herein can be used for medical applications, animal husbandry and veterinary applications. Typically, the product is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

Peptide and Metallo-Construct Molecule Libraries and Combinatorial Chemistries. There is an increasing emphasis on designing peptide, peptidomimetic, psuedo-peptide, and non-peptide organic molecular libraries that are highly biased in terms of structural and conformational diversity as well as specifically directed towards a particular biological target, such as specificity for one or more opioid receptors. In many applications, libraries of peptidomimetics and small organic molecules are preferred over peptide libraries because of considerations such as metabolic stability, bioavailability and pharmacokinetics. The prior art with respect to libraries and combinatorial chemistry has not addressed or explored the area of metallopeptides and metallo-construct molecules. Metal complexed to a suitably designed peptide or organic molecule so as to satisfy the metal coordination sphere leads to highly constrained structures, with significant advantages in specificity, affinity, metabolic stability, bioavailability and pharmacokinetics.

Using the methods of this invention, libraries of peptides designed to specifically bind one or more opioid receptors are provided wherein each constituent peptide includes an amino acid sequence necessary for providing a coordination site for complexation with a metal ion, it being understood that such amino acid sequence may differ among the constituent peptide members of the library. Upon complexing the peptides forming the library with a metal ion, a specific structure results, forming a mimic of a reverse turn structure. The specific stereochemical features of this peptide-metal ion complex are due to the stereochemistry of the coordination sphere of the complexing metal ion. Thus, the preferred geometry of the coordination sphere of the metal ion dictates and defines the nature and extent of the conformational restriction imposed on the peptide.

One application of this invention is the use of either locally or globally constrained metallopeptide structures as templates to assemble libraries. Libraries of metallopeptides may include molecules with either local conformation restrictions or global conformation restrictions, or some combination thereof. This aspect of the invention includes a variety of methods of synthesis, screening and structural elucidation of positive hits in screening systems. The importance of these aspects is well known to those skilled in the art and will also become evident from the following description and examples.

In general, most of the metal ions that may prove useful in this invention have a coordination number of 4 to 6, and rarely as high as 8, which implies that the putative metal ion-binding amino acid sequence must be made of residues with reactive groups located in a stereocompatible manner so as to establish a bond with a metal ion of given geometry and coordination sphere. Coordinating groups in the peptide chain include nitrogen atoms of amine, amide, imidazole, or guanidino functionalities; sulfur atoms of thiols or disulfides; and oxygen atoms of hydroxy, phenolic, carbonyl, or carboxyl functionalities. In addition, the peptide chain or individual amino acids can be chemically altered to include a coordinating group, such as oxime, hydrazino, sulfhydryl, phosphate, cyano, pyridino, piperidino, or morpholino groups. For a metal with a coordination number of 4, either a tetrapeptide amino acid sequence may be employed (such as Gly-Gly-Gly-Gly (SEQ ID NO:1)); or, a tripeptide amino acid sequence in which at least one of the amino acids has a side chain with a coordinating group can similarly be employed (such as Gly-Gly-Cys). The side chain can have a nitrogen, oxygen or sulfur-based coordination group. Thus, an amino acid sequence can provide an $N_4$, $N_3S_1$, $N_2S_2$, $N_1S_3$, $N_2S_1O$ or similar ligand yielding tetradentate coordination of a metal ion utilizing nitrogen, sulfur and oxygen atoms.

In another embodiment of the invention, the metal ion-binding amino acid sequence may include one or more amino acid residues and one or more derivatized amino acids or spacer sequences, with the derivatized amino acid or spacer sequence having a nitrogen, sulfur or oxygen atom available for complexing with the various oxidation states of the metal. Examples of derivatized amino acids include amide, primary alkyl or aryl amide, 1,2,3,4-tetrahydroisoquinoline-2-carboxylic acid and its corresponding 7-hydroxy derivative, N-carboxymethylated amino acids, 2'-mercapto-Trp, Nβ-(2 mercaptoethane)-α,β-diaminopropionic acid and similar higher homologs of other homologous amino acids, Nβ-(2 aminoethane)-α,β-diaminopropionic acid and similar higher homologs of other homologous amino acids, Nβ-(picolinoyl)-α,β-diaminopropionic acid and similar higher homologs of other homologous amino acids, β-(picolylamide)-Asp and similar homologs of other homologous amino acids, Nβ-(2-amino-benzoyl)-α,β-diaminopropionic acid and similar higher homologs of other homologous amino acids, β-(2-amidomethylpyridine)-Asp and similar homologs of other homologous amino acids, N-benzyloxycarbonyl amino acid, N-tert butyloxycarbonyl amino acid, N-fluorenylmethyloxycarbonyl amino acid and other similar urethane-protected amino acid derivatives, and other derivatized or synthetic amino acids relating to any of the foregoing. Examples of spacer sequences which may be employed in this invention include 2mercaptoethylamine, succinic acid, glutaric acid, 2-mercaptosuccinic acid, ethylenediamine, diethylenetriamine, triethylenetetraamine, tetraethylenepentaamine, glycol, polyethylene glycol, thioglycolic acid, mercaptopropionic acid, pyridine-2-carboxylate, picolylamine, 2-mercaptoaniline, 2-aminobenzoic acid, and 2-aminomethylpyridine. In general, any sequence which may be linked, directly or indirectly, to two amino acids so as to form a continuous sequence, and which has a nitrogen, sulfur or oxygen atom available for complexing with the valences of the metal ion, may be employed.

The complexation of metal ions to the peptides in a library, and specifically to the metal ion-binding amino acid sequence of the peptide, is achieved by mixing the peptides with the metal ion. This is conveniently done in solution, with the solution including an appropriate buffer. In one approach, the metal ion is, when mixed with the peptide, already in the oxidation state required for complexing to the metal ion-complexing backbone. Some metal ions are complexed in their most stable oxidation state, such as ionic forms of calcium, potassium, indium, manganese, copper, zinc, cobalt and other metals. In another approach, the metal ions must be reduced to a lower oxidation state in order to be complexed to the metal ion-complexing backbone. This is true of ferric, stannic, pertechnetate, perrhenate and other similar metal ions. Reduction may be performed prior to mixing with the peptides, simultaneously with mixing with the peptides, or subsequent to mixing with the peptides. Any means of reduction of metal ions to the desired oxidation state known to the art may be employed.

In one embodiment of this invention, a library is provided in which the metal ion-binding amino acid sequence in the peptides forms a reverse turn structure upon complexation with a metal ion, with the library constructed such that side chains of amino acids within the metal ion-binding sequence are varied, and similarly amino acids not forming a part of the metal ion-binding sequence are also varied. Various compounds in a library of metallopeptides can be obtained by varying the sequence of amino acids in a set of peptides that are all optimized to form a complex of nearly similar geometry when coordinated with a metal ion. This optimization can be obtained, for example, by appropriate positioning of amino acids having high affinity to complex a metal ion. Examples of naturally occurring amino acids with high affinity for metal complexation include Cys and His. A library of such peptides, therefore, would have at least one of these amino acids that is suitably placed in the sequence, with this amino acid being common to all the molecules in the library, and thus with this amino acid non-randomized.

A conceptual, generalized view of a solid phase library of metallopeptides that is constructed using local conformational restriction is:

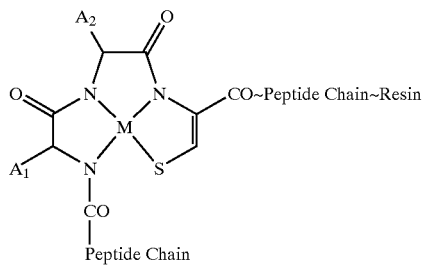

where M is a metal ion, $A_1$ and $A_2$ are amino acid side chains forming parts of the reverse turn structure which is the potential biological-function domain, and "Peptide Chain" denotes one or more amino acids. A similar library can also be constructed in which the components are in solution, and thus not bound to a resin.

The functional equivalent of each these peptide libraries may also be obtained through the development of a library of non-amino acid building blocks so as to result in structural mimics of these peptides. The peptide bonds may be replaced by pseudopeptide bonds, such as thioamides, thioethers, substituted amines, carbonate, urethane, aliphatic moieties, and functionally similar constructs.

A peptide library is first assembled according to the sequence specification and degeneration, as described above, by well-known methods of peptide synthesis. These libraries can be synthesized as discreet, spatially addressable compounds in parallel synthesis, or by using split synthesis approaches, or by deconvolution techniques of soluble libraries. Using similar methods, a pseudopeptide, peptidomimetic or non-peptide library can be obtained. The non-peptide libraries may also incorporate one of various tagging approaches that are well known to those skilled in the art. Both solid-phase and soluble libraries can be obtained in this manner. The entire library is then reacted with an appropriate metal-complexing agent to obtain the corresponding metal-coordinated library, comprising a similar class of predetermined structures. For example, to complex a peptide library with rheniumoxo metal ion, the peptide library can be treated with oxotrichlorobis(triphenylphosphine) rheniumm in the presence of sodium acetate. This procedure results in quantitative complexation of ReOM with the peptide. In order to complex Zn, Co, Mn, Fe or Cu ions, the peptide library is treated with chloride or other suitable salts of these metal ions to yield the library of corresponding metal ions. Essentially, a variety of metal ions can be used to construct different metallopeptide libraries. One factor considered in selection of the appropriate metal ion is the relative stability of a particular metal-peptide complex, which is related in large part to the metal-peptide binding constant or constants. It is well known in the art that some metal-peptide constructs are stable only within specified pH or other special conditions, or are easily oxidized in air. Other peptide-metal ion complexes, such as those with ReOM, are stable in pure form and can be isolated and stored under normal storage conditions for a long period of time.

A metallopeptide library constructed according to this invention can be screened to identify one or more candidates that specifically bind one or more opioid receptors by various techniques that have been reported in the prior art. Both soluble and solid phase libraries may be directly employed in these assays.

Among these techniques, the deconvolution and iterative resynthesis approach, the approach involving orthogonal pools of two co-synthesized libraries, and the positional scanning method may be directly applied to soluble metallopeptide libraries to elucidate the structure of a "hit," or peptide identified as a candidate for specifically binding one or more opioid receptors in the screening process. For solid phase libraries, other than spatially addressable parallel synthesis libraries, the structure of hits can be directly determined by various strategies now well known to those skilled in the art.

S-Protected Thiol Group Compounds in Metallo-Libraries. A free thiol (—SH) group is preferred for complexation of most metal ions to the peptides of this invention, and in many cases a —SH group is necessary in order to form a stable exchange-inert complex with a metal ion. Peptides and other organic molecules with free —SH groups, however, are easily oxidized in air and in solution, and can often form a disulfide-linked dimer. If more than one free —SH group is present in a molecule, oxidation may lead to a complex polymer. Similarly, if a mixture of different peptides or organic molecules with free —SH groups is prepared, oxidation generally leads to a complex mixture of polymers of unknown composition. This is of serious concern in preparing libraries of metallopeptides or other organic molecules where one or more —SH group is intended for use in metal complexation.

A variety of —SH protecting groups have been employed for different purposes, including radiopharmaceutical manufacture and formulation. For example, in its protected form S-Benzoyl-mercaptoacetyl-glycyl-glycyl-glycine (Bz-MAG$_3$) has been used to complex Tc-99m ($^{99m}$Tc) under conditions where the S-Bz group splits during $^{99m}$Tc complexation. The use of S-Bz protection, however, is not compatible with the methods of peptide synthesis.

In order to construct metallopeptide libraries of this invention which incorporate an —SH group, if mixed pool synthesis is employed the peptides must be S-protected derivatives. The —SH protecting group is chosen such that (a) the synthesis of peptide derivatives with S-protecting group is compatible with methods of solution and solid phase peptide synthesis, so that the S-protecting group is stable during synthetic procedures, and (b) the S-protecting group can be deprotected in situ, without cleavage from the resin in the case of solid phase synthesis, during the metal complexation step. Many prior art methods, such as Bz-MAG$_3$, meet at most only one of the two criteria specified above (for example, Bz-MAG$_3$ meets only criterion "b").

Use of orthogonally S-protected thiol groups permits synthesis of metallo-compounds in a single pot. A mixture of compounds, each compound containing an orthogonally S-protected group, is used for complexation with a metal ion, and it is only during metal ion complexation that the S-protected group is deprotected, and accordingly polymerization and cross-linking is avoided. This procedure thus provides homogenous libraries of metallo-compounds.

One S-protected thiol group meeting the criteria specified above, and which can be used in this invention, employs an S$^t$Bu (S-thio-butyl or S-t-butyl) group to protect the —SH group. The S$^t$Bu group is stable under both the acidic and basic conditions typically employed in peptide synthesis. Further, the S$^t$Bu group may be cleaved by reduction using a suitable phosphine reagent, which reduction step may be employed immediately prior to or in conjunction with complexation of a metal ion to the peptide. Such cleavage does not cleave the peptide from the resin, or otherwise alter the structure of the peptide.

Another S-protecting group meeting the criteria specified above and suitable for this invention employs an S-Acm (S-acetamidomethyl) group to protect the —SH group. The Acm group is also stable under the acid and base conditions usually employed during peptide synthesis. The S-Acm group may be removed by treatment of S-Acm-protected peptide or peptide resin with mercury (II) acetate or silver (I) tertrafluoroborate, which liberates the thiol peptide in its mercury or silver ion-complexed state. Free thiol-containing peptide can then be recovered by treating the mercury or silver ion and thiol complexed salts with an excess of a thiol-containing reagent, such as beta-mercaptoethanol or dithiothreitol. The resulting peptide is then used for metal complexation. Alternatively, the mercury or silver ion and thiol complexed peptide may be directly treated with a metal ion complexing reagent to form the desired metallopeptide.

Other examples of S-protecting groups meeting suitability in the synthetic scheme for metallopeptides include 4-methoxytrityl (Mmt) and 3-nitro-2-pyridinesulfenyl (Npys) and S-sulfonate (SO$_3$H). Mmt is selectively removed upon treatment with 1% TFA in dichloromethane. Npys and S-sulfonate are selectively removed by treatment with a thiol-containing reagent such as beta-mercaptoethanol or dithiothreitol or a phosphine reagent such as tributyl phosphine. The Npys group (Simmonds R G et al: *Int J Peptide Protein Res* 43:363, 1994) is compatible with Boc chemistry for peptide synthesis and S-sulfonate (Maugras I et al: *Int J Peptide Protein Res* 45:152, 1995) is compatible with both Fmoc and Boc chemistries. Similar protecting groups derived from homologous series of S-alkyl, or S-aryl, or S-aralkyl may also be used in this invention. A primary characterization of the protecting group is that its use results in the formation of a disulfide (S—S) bond utilizing one sulfur atom each from the thiol-containing amino acid and the protecting group. In addition, the resulting disulfide (S—S) bond is cleavable by the use of any of a variety of disulfide cleaving agents, including but not limited to phosphine- and thiol-containing reagents.

The method employing S$^t$Bu protected —SH groups, or other protecting groups that afford orthogonal deprotection, may be employed for the generation of either solid phase or soluble libraries. For solid phase libraries, peptides may be synthesized by use of conventional Fmoc chemistry. In the case of conventional Fmoc chemistry, Fmoc-L-Cys-(S$^t$Bu) is coupled to an appropriate resin, via one or more intermediate amino acids, and additional amino acids are thereafter coupled to the L-Cys-(S$^t$Bu) residue. S$^t$Bu may be employed with either L- or D-Cys, and any of a variety of other amino acids, including designer or unnatural amino acids and mimics thereof, characterized by possession an —SH group available for binding to a metal ion, including, but not limited to, 3-mercapto phenylananine and other related 3-mercapto amino acids such as 3-mercapto valine (penicillamine); 2-mercaptoacetic acid; 3-mercaptopropionic acid; 2mercaptopropionic acid; 3-mercapto-3,3,-dimethyl propionic acid; 3-mercapto,3-methyl propionic acid; 3-mercapto-3,3,-diethyl proprionic acid; 2-mercapto,2-methyl acetic acid; 3-cyclopentamethlene,3-mercaptopropionic acid; 2-cyclopentamethlene,2-mercaptoacetic acid and related amino acids. In all these cases, S-protection can be by StBu, S-Acm, Mmt, Npys, S-sulfonate and related groups, as described above.

In another embodiment of this invention, there are provided methods for complexing a metal ion to the component members of a peptide combinatorial library as described above, which library may be a soluble or solid phase peptide library. This provides a method for complexing substantially all of the available peptides with a metal ion, so that each component member is conformationally constrained as a result of the metal ion complexation, thereby resulting in a specific and unique conformationally constrained domain. For tetradentate coordination with a non-radioactive metal ion, rhenium is a preferred ion. Solid phase resin bound peptides may be complexed with rhenium ion by treatment with the rhenium transfer agent ReO[V]Cl$_3$(PPh$_3$)$_2$ in the presence of 1,8-Diazabicyclo[5,4,0]undec-7-ene (DBU) as a base. The peptides may then be cleaved from the resin. Alternatively, peptides in a soluble library may similarly be complexed by treatment with the rhenium transfer agent ReO[V]Cl$_3$(PPh$_3$)$_2$ in the presence of DBU as a base. Metal complexation in the presence of DBU as a base can conveniently be accomplished at ambient room temperature.

In an alternative method of metal complexation a mild base, such as sodium acetate, can be used. In this case the thiol-containing peptide-resin or free peptide is taken in a suitable solvent, such as DMF, NMP, MeOH, DCM or a mixture thereof, and heated to approximately 60–70° C. with the rhenium transfer agent ReO[V]Cl$_3$(PPh$_3$)$_2$ in the presence of sodium acetate for a suitable time, such as 15 minutes. Similarly, other bases such as triethylamine, ammonium hydroxide and so on, may be employed. According to this invention, MeOH is a preferred choice of solvent for rhenium complexation in the case of S-deprotected peptides in solution. The solvent choice for S-deprotected peptides still attached to the solid phase is guided mainly by considerations of superior solvation (swelling) of the solid phase. DMF and NMP generally are used. Various mixtures of these solvents, also in combination with MeOH or DCM, such as CHCl$_3$ and so on, may also be employed to yield optimized complexation results.

In one embodiment of this invention, an S$^t$Bu protected peptide is treated in situ with rhenium transfer agent in the presence of DBU and tributylphosphine to effect S-deprotection and rhenium complexation in one pot. Alternately, complexation of rhenium to the S$^t$Bu protected peptide in the presence of rhenium perrhenate may be accomplished by treatment with Sn[II]Cl$_2$. This reagent effects S-deprotection as well as conversion of ReO$_4$[VII] state to ReO[V] state in situ to cause complexation of the rhenium to the S-deprotected peptide. A preferred procedure in this invention is the use of S$^t$Bu protected peptide with S-deprotection by treatment with tributylphosphine, and metal complexation of the resulting peptide utilizing ReO[V]Cl$_3$(PPh$_3$)$_2$ in the presence of DBU at room temperature.

Opioid Receptor-Specific Agents. This invention includes a δ opiate receptor-specific metallopeptide for use as a therapeutic agent for pain management. The δ receptor-specific ligand is a safer, antinociceptive agent than currently used drugs that act primarily through μ receptor and exhibit unwanted side effects such as addiction, tolerance, depression of cardiovascular and respiratory functions, and constipation. The invention is based on metallopeptides containing an opioid peptide pharmacophore modeled on Tyr-(X)$_n$-Phe; where X is an optional amino acid residue or mimic thereof for positioning the biologically important Tyr and Phe residues, and n is from 0 to about 4. These are metallopeptides in which a three to five amino acid sequence is complexed to a metal ion to form a conformationally restricted structure mimicking a reverse turn that is characteristic of the pharmacophore for opioid peptides. Side chains and chirality of the amino acid residues within the sequence, and other amino acids and groups forming the structure, can be changed to produce a wide range of structural diversity within narrowly specified reverse turn parameters. In addition, the metallopeptide reverse turn can also incorporate amino acids that normally have a low propensity to exist in a turn motif.

These metallopeptides are conceptually designed around a minimal tripeptide sequence binding a rhenium metal ion by, in one preferred embodiment, an N$_3$S$_1$ ligand. Alternatively, an N$_2$S$_2$ ligand may be employed. A variety of peptide analogs selective for one or another of opioid receptors have been developed and all exhibit a characteristic reverse turn structure, and are primarily of the general message segment structure Tyr-[X]$_n$-Phe as described above. This reverse turn conformation makes opioid peptides good candidates for mimicking in metallopeptide format. Putative opioid metallopetides can be obtained by functionalizing the metal-binding sequence, generally a tri-peptide, with Tyr- and Phe-like message segment residues. In addition, the tyramine moiety can be precisely positioned with respect to the phenyl ring of Phe. For example, a phenol-phenyl distance of 7±1.5 Å for δ receptor ligands has been reported, and can be utilized using the method and compounds of this invention. These geometric considerations, along with further stereochemical refinements, including but not limited to the chirality of amino acid side-chains, can also be utilized in the ligand design process.

A presumptive opioid metallopeptide design is based on the opioid pharmacophore Tyr-[X]$_n$-Phe-Y; where X, if present, is one or more amino acid residues positioning the biologically important Tyr and Phe residues, which include message elements, in the required spatial arrangement; n is from 0 to about 4, and Y is an amino acid residue that may potentiate biological activity, including an address element. Various SAR, conformational (NMR), and computational studies have shown that this pharmacophore exists as a reverse turn for all μ, δ, and κ opiate receptor subtypes. It is widely viewed that the relative receptor selectivities of opioid ligands depend on preferred conformational subtleties within this reverse turn motif, making it suitable for conversion into a metallopeptide format. In this approach metallopeptides are designed around a base tri-peptide metal binding sequence which strongly binds a rhenium metal ion. This rhenium metal-tri-peptide scaffold is derivatized in alternative manners, such as with either the Tyr or the Phe residue constrained within the metal ion coordination sphere. For example, two base metallopeptide constructs as putative candidates for opioid receptors are Tyr-Cys-[Gly-Phe-Cys]—NH$_2$ (SEQ ID NO:2):

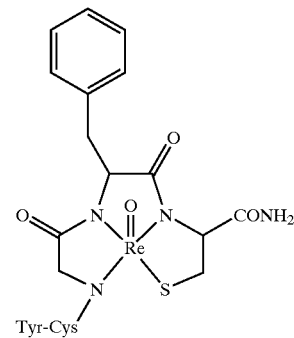

and [Tyr-D-Lys-Cys]-Phe:

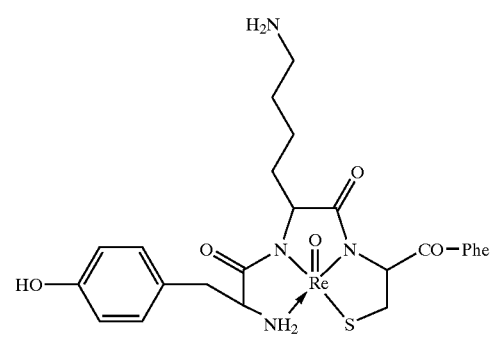

Based on this approach, series of metallopeptides have been defined relating to opioid receptor-specific agents. This invention thus provides a discrete series of peptides of the following formulas:

R$_1$—R$_2$—R$_3$—R$_4$    Formula I wherein
R₁ is an L- or D-amino acid with a phenol moiety side chain, and with an —N available for complexation to a metal ion. Representative amino acids include, but are not limited to, L- or D-configurations of Tyr, homoTyr, p-hydroxy-phenylglycine, and N-alkylated, N-arylated, or N-aralkylated derivatives of Tyr, homoTyr, or p-hydroxy-phenylglycine. Other synthetic derivatives may also be employed, such as Ser(O-(p-hydroxy)benzyl), Thr(O-(p-hydroxy)benzyl), Cys(S-(p-hydroxy)benzyl), Lys(N-epsilon(p-hydroxy)phenyl), Lys(N-epsilon(p-hydroxy)benzyl) and related homologs. In a preferred embodiment the position of phenol hydroxyl group is para, but its position on the phenyl ring may also be ortho or meta.

R₂ is a neutral or basic L- or D-amino acid with an —N available for complexation to a metal ion. Representative amino acids include, but are not limited to, L- or D-configurations of Gly, Ala, Leu, Ile, Nle, Arg, Lys, Orn and homoArg, as well as other neutral or basic amino acids.

R₃ is L- or D-Cys, L- or D-homoCys, L- or D-Pen or a derivative or homolog of any of the foregoing, with both an —N and —SH available for complexation to a metal ion.

R₄ is a free carboxylate, primary amide or aryl or aralkyl chain substituted amide of R₃, or an L- or D-amino acid with a neutral aromatic side chain or side chain with an aromatic ring substituted halogen, nitro or alkyl group, or is a des-carboxyl derivative corresponding to such L- or D-amino acid. Representative amino acids include, but are not limited to, L- or D-configurations of Phe, homoPhe, Phg, NaI, Trp, Dip, Bip, Ser(O-benzyl), Thr(O-benzyl), Cys(S-benzyl) and related homologs, as well as des-carboxyl derivatives.

Upon complexation with a metal ion as described, the structure of the composition of Formula I is as follows (In this structural representation, partial structures of the amino acids involved in metal ion complexation are shown, with side chains and remaining portions of the amino acids designated by primed notations. The complete structure of amino acid R₃ involved in binding the metal ion through its N and S atoms is shown.):

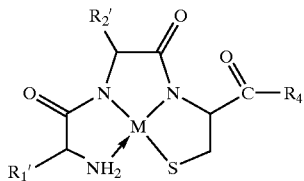

Representative peptides of Formula I include the following from Table 1: Tyr-Gly-Cys-Phe-NH₂ (SEQ ID NO:3); Tyr-Ala-Cys-HPhe-NH₂ (SEQ ID NO:6); Tyr-Ala-Cys-Phg-NH₂ (SEQ ID NO:7); Tyr-Ala-Cys-Phe-NH₂ (SEQ ID NO:8); Tyr-Gly-Cys-Phg-NH₂ (SEQ ID NO:9); Tyr-Gly-Cys-HPhe-NH₂ (SEQ ID NO:10); Tyr-D-Lys-Cys-Phe-NH₂; Tyr-D-Lys-Cys-Phe; Tyr-Val-Cys-Phe-NH₂ (SEQ ID NO:16); Phe-Tyr-Lys-Cys-NH₂ (SEQ ID NO:17); Tyr-Lys-Cys-OH and Tyr-D-Lys-Cys-OH.

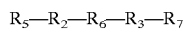 Formula II wherein
R₅ is an L- or D-amino acid with a phenol moiety side chain. Representative amino acids include, but are not limited to, L- or D-configurations of Tyr, homoTyr, p-hydroxy-phenylglycine, and N-alkylated, N-arylated, or N-aralkylated derivatives of Tyr, homoTyr, or p-hydroxy-phenylglycine, and corresponding des-amino acid derivatives of any of the foregoing. Other synthetic derivatives may also be employed, such as Ser (O-(p-hydroxy)benzyl), Thr(O-(p-hydroxy)benzyl), Cys(S-(p-hydroxy)benzyl), Lys(N-epsilon(p-hydroxy)phenyl), Lys(N-epsilon(p-hydroxy)benzyl) and related homologs, and corresponding des-amino acid derivatives of any of the foregoing. In a preferred embodiment the position of phenol hydroxyl group is para, but its position on the phenyl ring may also be ortho or meta.

R₂ is as defined above.

R₆ is an L- or D-amino acid with a neutral side chain or side chain with an aromatic ring substituted halogen, nitro or alkyl group, with an —N available for complexation to a metal ion. Representative amino acids include, but are not limited to, L- or D-configurations of Phe, homoPhe, Phg, NaI, Trp, Dip, Bip, Ser(O-benzyl), Thr(O-benzyl), Cys(S-benzyl) and related homologs.

R₃ is as defined above.

R₇ is a free carboxylate or terminal amide of R₃ or a neutral or basic L- or D-amino acid, or is a des-carboxyl derivative corresponding to such L- or D-amino acid. Representative amino acids include, but are not limited to, L- or D-configurations of Gly, Ala, Leu, Ile, Nle, Arg, Lys, Orn and homoArg, as well as other neutral or basic amino acids, and des-carboxyl derivatives of any of the foregoing.

Upon complexation with a metal ion as described, the structure of the composition of Formula II is as follows (In this structural representation, the partial structures of the amino acids involved in metal ion complexation are shown, with side chains and remaining portions of the amino acids designated by primed notations. The complete structure of amino acid R₃ involved in binding the metal ion through its N and S atoms is shown.):

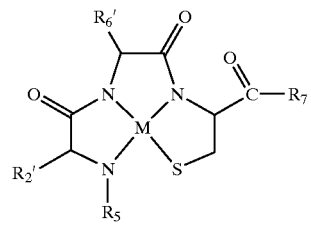

Representative peptides of Formula II include the following from Table 1: Tyr-Gly-Gly-Cys-Phe-NH₂ (SEQ ID NO:5); Tyr-Gly-D-Phe-Cys-NH₂; HTyr-Gly-Phe-D-Cys-NH₂; (p-OH)—C₆H₄—CO-Gly-Lys-D-Cys-NH₂; Tyr-Val-Phe-Cys-NH₂ (SEQ ID NO:15) and Tyr-Ala-Phe-Cys-OH (SEQ ID NO:18).

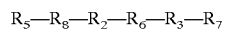 Formula III wherein
R₅ is as defined above.

R₈ is a neutral or basic L- or D-alpha or -omega amino acid, or is a derivative corresponding to such. Representative amino acids include, but are not limited to, L- or D-configurations of Gly, Ala, Leu, Ile, Nle, Phe, Lys, Orn, Abu, Dpr and other basic amino acids, di-basic amino acids incorporated through an alpha or omega amino group, and Cys. $R_8$ also includes amino acids such as β-Ala, and higher omega amino aliphatic carboxylic acid homologs. $R_8$ may include any neutral or basic L- or D-alpha or -omega amino acid with a free amino group that serves to facilitate electrostatic contact with the receptor.

$R_2$ is as defined above.
$R_6$ is as defined above.
$R_3$ is as defined above.
$R_7$ is as defined above.

Upon complexation with a metal ion as described, the structure of the composition of Formula II is as follows (In this structural representation, the partial structures of the amino acids involved in metal ion complexation are shown, with side chains and remaining portions of the amino acids designated by primed notations. The complete structure of amino acid $R_3$ involved in binding the metal ion through its N and S atoms is shown.):

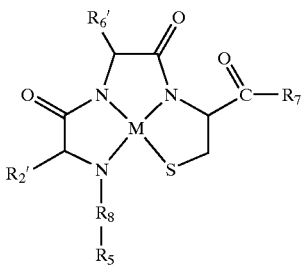

Representative peptides of Formula III include the following from Table 1: Tyr-Ala-Gly-Phe-Cys-NH$_2$ (SEQ ID NO:4); Tyr-Cys-Gly-Phe-Cys-NH$_2$(SEQ ID NO:2); Tyr-β-Ala-Gly-Phe-Cys-NH$_2$ (SEQ ID NO:11); Tyr-β-Ala-Gly-Phe-D-Cys-NH$_2$; HTyr-β-Ala-Gly-Phe-Cys-NH$_2$ (SEQ ID NO:12); HTyr-β-Ala-Gly-Phe-D-Cys-NH$_2$; Tyr-β-Ala-Phe-Gly-Cys-OH (SEQ ID NO:20) and Tyr-[NH(CH$_2$)$_3$—CH (NH$_2$)—CO]-Gly-Phe-D-Cys-NH$_2$.

$$R_9—R_1—R_3—R_{10} \quad \text{Formula IV}$$

wherein $R_9$ is an L- or D-amino acid with a basic functional group side chain and with an —N available for complexation to a metal ion. Representative amino acids include, but are not limited to, L- or D-configurations of Arg, Lys, Orn, homoArg, Abu, Dpr or other basic amino acids.

$R_1$ is as defined above.
$R_3$ is as defined above.
$R_{10}$ is a free carboxylate, primary amide or aryl or aralkyl chain substituted amide of $R_3$, or an L- or D-amino acid with a neutral aromatic side chain or side chain with a ring substituted halogen, nitro or alkyl group. Representative amino acids include, but are not limited to, L- or D-configurations of Phe, homoPhe, Phg, NaI, Trp, Dip, Bip, Ser(O-benzyl), Thr(O-benzyl), Cys(S-benzyl) and related homologs, including those wherein the aromatic ring is substituted with a halogen, nitro or alkyl group, as well as des-carboxyl derivatives of any of the foregoing.

Upon complexation with a metal ion as described, the structure of the composition of Formula IV is as follows (In this structural representation, the partial structures of the amino acids involved in metal ion complexation are shown, with side chains and remaining portions of the amino acids designated by primed notations. The complete structure of amino acid $R_3$ involved in binding the metal ion through its N and S atoms is shown.):

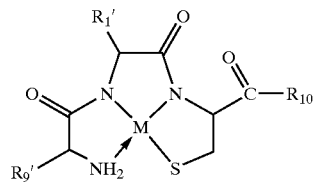

Representative peptides of Formula IV include the following from Table 1: Lys-Tyr-Cys-OH and D-Lys-Tyr-Cys-OH.

$$R_5—R_{11}—R_6—R_{12} \quad \text{Formula V}$$

wherein $R_5$ is as defined above.
$R_{11}$ is L- or D-Cys, L- or D-homoCys, L- or D-Pen or a derivative or homolog of any of the foregoing, with an —SH available for complexation to a metal ion.
$R_5$ is as defined above.
$R_{12}$ is a neutral L- or D-amino acid with an —N available for complexation to a metal ion, and with a terminal amide with an —N available for complexation to a metal ion. Representative amino acid amides include, but are not limited to, L- or D-configurations of a neutral amino acid such as Gly, Ala, Leu, Ile, Nle, Phe, or a related amino acid with a terminal amide.

Upon complexation with a metal ion as described, the structure of the composition of Formula V is as follows (In this structural representation, the partial structures of the amino acids involved in metal ion complexation are shown, with side chains and remaining portions of the amino acids designated by primed notations. The complete structure of amino acid $R_1$, involved in binding the metal ion through its S atom is shown.):

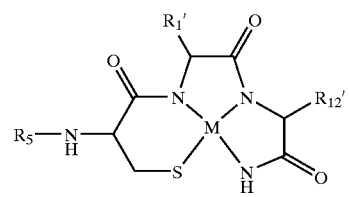

Representative peptides of Formula V include Tyr-Cys-D-Phe-Gly-NH$_2$ from Table 1.

$$R_5—R_1, —R_{13}—R_3—R_{10} \quad \text{Formula VI}$$

wherein $R_5$ is as defined above.
$R_{11}$ is as defined above.
$R_{13}$ is an L- or D-amino acid with a neutral aliphatic or aromatic side chain or side chain with a ring substituted halogen, nitro or alkyl group, with an —N available for complexation to a metal ion. Representative amino acids include, but are not limited to, L- or D-configurations of Gly, Ala, Nle, Val, Leu Phe, homoPhe, Phg, NaI, Trp, Dip, Bip, Ser(O-benzyl), Thr(O-benzyl), Cys (S-benzyl) and related homologs.
$R_3$ is as defined above.
$R_{10}$ is as defined above.

Upon complexation with a metal ion as described, the structure of the composition of Formula VI is as follows (In this structural representation, the partial structures of the amino acid $R_{13}$ involved in metal ion complexation are shown, with side chains and remaining portions of the amino acid designated by primed notations. The complete structure of amino acid $R_3$ involved in binding the metal ion through its N and S atoms is shown, as is the complete structure of amino acid $R_{11}$ involved in binding the metal ion through its S atom.):

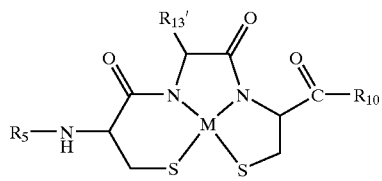

Representative peptides of Formula VI include Tyr-Cys-Gly-Cys-NH$_2$ (SEQ ID NO:19) from Table 1.

$$R_{14}—R_6—R_{16}—R_3—R_{16} \qquad \text{Formula VII}$$

wherein $R_{14}$ is a neutral or basic L- or D-alpha or -omega amino acid, or is a derivative corresponding to such. Representative amino acids include, but are not limited to, L- or D-configurations of Gly, Ala, Leu, Ile, Nle, Phe, Trp, Lys, Orn, Abu, Dpr and other di-basic amino acids, and amino acids such as beta-Ala and higher omega amino acids with a free amino group that serves to facilitate electrostatic contact with the receptor.

$R_6$ is as defined above.

$R_{15}$ is a L- or D-amino acid with an —N available for complexation to a metal ion and hydrogen bond forming groups in the side chain. Representative amino acids include, but are not limited to, Ser, Thr, Asp, Glu, Lys, Orn, Arg and homoArg.

$R_3$ is as defined above.

$R_{16}$ an L- or D-amino acid with a phenol moiety side chain. Representative amino acids include, but are not limited to, Tyr, homoTyr, p-hydroxy-phenylglycine, their corresponding amide and des-carboxy derivatives. Other synthetic derivatives with the defied structural features may also be employed, such as Ser(O-(p-hydroxy)benzyl), Thr(O-(p-hydroxy)benzyl), Cys(O-(p-hydroxy)benzyl), Lys(N-epsilon(p-hydroxy)phenyl), Lys(N-epsilon(p-hydroxy)benzyl) and related homologs, and corresponding amide and des-carboxy derivatives. In a preferred embodiment the positions of phenol hydroxyl group is para, but its position on the phenyl ring may also be ortho or meta.

Upon complexation with a metal ion as described, the structure of the composition of Formula VII is as follows (In this structural representation, the partial structures of the amino acids involved in metal ion complexation are shown, with side chains and remaining portions of the amino acids designated by primed notations. The complete structure of amino acid $R_3$ involved in binding the metal ion through its N and S atoms is shown.):

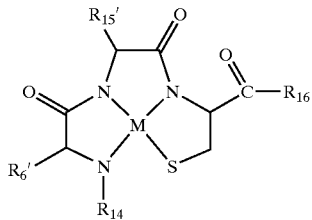

Representative peptides of Formula VII include NH$_2$(CH$_2$)$_4$—CO—HPhe-Asp-Cys-HTyr-NH$_2$ (SEQ ID NO:14) and NH$_2$(CH$_2$)$_4$—CO-Phe-Asp-Cys-HTyr-NH$_2$ (SEQ ID NO:13) from Table 1.

Utility in Pharmaceutical Preparations. The metallopeptides of this invention may be used in pharmaceutical preparations according to methods well known in the art. Thus δ-selective opiate receptor agonists may be used for pain management, with decreased addiction potential (Rapake R and Porereca F. Development of delta opioid peptides as nonaddicting analgesics. *Pharm Res* 8:17, 1991). Such uses may be in combination with use of morphine or other antinociceptin agents, and may potentiate morphine and other agents, allowing administration of decreased doses of morphine. δ-selective opiate receptor antagonists may be used to treat morphine addiction and decrease tolerance and dependence on morphine, and may be helpful in treating alcoholism, drug addiction, including cocaine, and the like. δ-selective opiate receptor antagonists also exhibit immunosuppressive effects (Cheido M et al. Involvement of delta opioid receptors in immunosuppression. *Int J Neurosci* 263:207–211, 1994), and may be used for the treatment of autoimmune disorders, organ rejection upon transplantation, graft rejection and the like. κ-selective opiate receptor agonists may be used for pain management and conditions such as inflammation, pruritus, psoriasis and irritable bowel syndrome. κ-selective opiate receptor antagonists may be used for pathologies where selective κ opioid receptor blockade is desired, including appetite suppression and antipsychotic treatment; and μ-selective opiate receptor metallopeptides may be used for pain management, gastrointestinal disorders and the like. It is also possible and contempated that combinations can be employed, such as a δ-selective opiate receptor agonist or antagonist in combination with a μ-selective opiate receptor agonist, thereby increasing the efficacy of the U-selective opiate receptor agonist at minimal doses, and with the benefits of the δ-selective opiate receptor metallopeptide. In general, there are a large number of conditions for which agonist, antagonist or mixed agonist and antagonist opiate receptor-specific agents may be employed. The person skilled in the art will readily find additional pharmacological uses of selected metallopeptides of the present invention that are related to their properties as agonists, partial agonists or antagonists to specified opiate receptors.

Pharmaceutically acceptable salts of the metallopeptides of this invention may be formed by reaction with an appropriate acid. Acid addition salts of the compounds of this invention are prepared in a suitable solvent from the peptide and an excess of an acid, such as hydrochloric, hydrobromic, sulfuric, phosphoric, acetic, citric, lactic, tartaric, oxalic, trifluoroacetic, maleic, succinic and methanesulfonic, and other suitable acids known to persons skilled in the art.

The invention provides a pharmaceutical composition that includes a metallopeptide of this invention and a pharmaceutically acceptable carrier. The carrier may be a liquid formulation, and is preferably a buffered, isotonic, aqueous solution. Pharmaceutically acceptable carriers also include excipients, such as diluents, carriers and the like, and additives, such as stabilizing agents, preservatives, solubilizing agents, buffers and the like.

The metallopeptides of this invention are less susceptible to protease and other enzymatic degradation than are conventional peptides, and may be administered by means other than by injection. The metallopeptides of this invention may be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, antioxidants and other agents known in the art. In general, any route of administration by which the metallopeptides of this invention are introduced across an epidermal layer of cells may be employed. Administration means may include administration through mucous membranes, buccal administration, oral administration, dermal administration, rectal administration, sublingual administration, inhalation administration, nasal administration and the like.

The metallopeptides of this invention may be formulated or compounded into pharmaceutical compositions that include at least one metallopeptide of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, manniton, sodium chloride or sodium citrate. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release, sustained-release, or time-release formulations and additives may be employed, so that the dosage may be formulated so as to effect delivery of a metallopeptide of this invention over a period of time.

If a metallopeptide of this invention is administered by injection, the injection may be intravenous, subcutaneous, intramuscular, intraperitoneal or other means known in the art. For injection or other liquid administration formulations, water containing at least one or more buffering constituents is preferred, and stabilizing agents, preservatives and solubilizing agents may also be employed.

In general, the actual quantity of metallopeptides of this invention administered to a patient will vary between fairly wide ranges depending upon the specific metallopeptide, the mode of administration, the formulation used, and the response desired. In one embodiment, from about 1 $\mu$g to about 1 mg of metallopeptide per kg of body weight is administered per day.

The invention is further illustrated by the following non-limiting examples.

EXAMPLE 1

The peptide sequences of Table 1 were synthesized and complexed to rhenium metal ions. The resulting metallopeptides were assayed in the guinea pig ileum (GPI) and mouse vas deferens (MVD) in vitro functional assays for measuring functional (agonist or antagonist) activity mediated by $\mu$ and $\delta$ receptors, respectively. Selected metallopeptides of Table 1 were also assayed in equilibrium receptor-binding assays designed for $\mu$, $\delta$ and $\kappa$ opiate receptors using $^3$H-DAMGO ($\mu$ selective) and $^3$H-DSLET ($\delta$ selective) radioligands in the rat brain membrane binding assay and an $^3$H-U69593 ($\kappa$ selective) radioligand in the guinea-pig brain membrane binding assay. The results of these assays are shown in Table 1.

TABLE 1

| | In Vitro Functional Assay | | Receptor Binding Assay [Ki in $\mu$M] | | |
| --- | --- | --- | --- | --- | --- |
| | [ED$_{50}$ in $\mu$M] | | Mu | Delta | Kappa |
| Primary Structure | GPI | MVD | Receptor | Receptor | Receptor |
| Leu-Enkephalin (Reference compound) | 0.246 ± 0.039 | 0.0114 ± 0.0011 | 0.00253 ± 0.000035 | 0.00943 ± 0.00207 | 0.00214 ± 0.0002 |
| Tyr-Gly-Cys-Phe-NH$_2$ (SEQ ID NO:3) | >10 $\mu$M | 1.35 ± 0.34 | IA | | |
| Tyr-Ala-Gly-Phe-Cys-NH$_2$ (SEQ ID NO:4) | >10 $\mu$M | >10 $\mu$M | IA | IA | |
| Tyr-Cys-Gly-Phe-Cys-NH$_2$ (SEQ ID NO:2) | 0.612 ± 0.049 | 1.47 ± 0.11 | IA | 0.272 ± 0.004 | 2.1 ± 0.12 |
| Tyr-Gly-Gly-Cys-Phe-NH$_2$ (SEQ ID NO:5) | >10 $\mu$M | >10 $\mu$M | IA | IA | |
| Tyr-Cys-D-Phe-Gly-NH$_2$ | >10 $\mu$M | >10 $\mu$M | IA | IA | |
| Tyr-Gly-D-Phe-Cys-NH$_2$ | >10 $\mu$M | >10 $\mu$M | IA | IA | |
| Tyr-Ala-Cys-HPhe-NH$_2$ (SEQ ID NO:6) | WPA | WPA | | | |
| Tyr-Ala-Cys-Phg-NH$_2$ (SEQ ID NO:7) | WPA | IA | | | |
| Tyr-Ala-Cys-Phe-NH$_2$ (SEQ ID NO:8) | WPA | WPA | | | |
| Tyr-Gly-Cys-Phg-NH$_2$ (SEQ ID NO:9) | WPA | WPA | | | |
| Tyr-Gly-Cys-HPhe-NH$_2$ (SEQ ID NO:10) | WPA | WPA | | | |
| Tyr-D-Lys-Cys-Phe-NH$_2$ | IA | IA | | | |
| Tyr-D-Lys-Cys-Phe | 3.03 ± 0.43 | IA | | | |
| Tyr-$\beta$-Ala-Gly-Phe-Cys-NH$_2$ (SEQ ID NO:11) | IA | PA [22%] | | | |
| Tyr-$\beta$-Ala-Gly-Phe-D-Cys-NH$_2$ | IA | PA [30%] | | | |
| HTyr-$\beta$-Ala-Gly-Phe-Cys-NH$_2$ (SEQ ID NO:12) | IA | PA [30%] | | | |

TABLE 1-continued

| | In Vitro Functional Assay | | Receptor Binding Assay [Ki in μM] | | |
|---|---|---|---|---|---|
| | [ED$_{50}$ in μM] | | Mu | Delta | Kappa |
| Primary Structure | GPI | MVD | Receptor | Receptor | Receptor |
| HTyr-β-Ala-Gly-Phe-D-Cys-NH$_2$ | IA | PA [11%] | | | |
| NH$_2$(CH$_2$)$_4$—CO-Phe-Asp-Cys-HTyr-NH$_2$ (SEQ ID NO:13) | IA | PA [20%] | | | |
| (p-OH)—C$_6$H$_4$(CH$_2$)$_2$—NH—CO—CH(NH$_2$)—(CH$_2$)$_2$—CO-Gly-Phe-D-Cys-NH$_2$ | IA | PA [9%] | | | |
| NH$_2$(CH$_2$)$_4$—CO-HPhe-Asp-Cys-HTyr-NH$_2$ (SEQ ID NO:14) | IA | IA | | | |
| Tyr-[NH(CH$_2$)$_3$—CH(NH$_2$)—CO]-Gly-Phe-D-Cys-NH$_2$ | IA | IA | | | |
| HTyr-Gly-Phe-D-Cys-NH$_2$ | IA | IA | | | |
| (p-OH)—C$_6$H$_4$—CO-Gly-Lys-D-Cys-NH$_2$ | IA | IA | | | |
| Tyr-Val-Phe-Cys-NH$_2$ (SEQ ID NO:15) | IA | IA | | | |
| Tyr-Val-Cys-Phe-NH$_2$ (SEQ ID NO:16) | IA | 1.42 ± 0.21 [ED$_{30}$] | | | |
| Tyr-D-Ala-Cys-Phe-NH$_2$ | 3.06 ± 0.29 [ED$_{40}$] | PA [16%] | | | |
| Phe-Tyr-Lys-Cys-NH$_2$ (SEQ ID NO:17) | IA | IA | | | |
| Tyr-Ala-Phe-Cys-OH (SEQ ID NO:18) | PA [8%] | PA [48%] | | | |
| Tyr-Cys-Gly-Cys-NH$_2$ (SEQ ID NO:19) | PA [14%] | PA [34%] | | | |
| Lys-Tyr-Cys-OH | PA [34%] | PA [41%] | | | |
| D-Lys-Tyr-Cys-OH | PA [28%] | PA [18%] | | | |
| Tyr-Lys-Cys-OH | PA [41%] | PA [48%] | | | |
| Tyr-D-Lys-Cys-OH | PA [57%] | PA [9%] | | | |
| Tyr-β-Ala-Phe-Gly-Cys-OH (SEQ ID NO:20) | PA [51%] | PA [17%] | | | |

In Table 1, "IA" means inactive, "PA" means partial agonist, and "WPA" means weak partial agonist. Observed percent efficacy at 10 μM is shown in brackets.

The μ and δ opioid receptor affinities of the compounds of this invention were determined in binding assays based on displacement of μ and δ selective radioligands from rat brain membrane binding sites and κ receptor affinities are measured by displacement of a κ-selective radioligand from the guinea-pig membrane binding site. Male Sprague Dawley rats (300 grams) or male guinea-pig were decapitated and after removal of cerebellum, the brains were homogenized in 30 volumes of ice-cold standard buffer (50 mM Tris-HCl, pH 7.7). After centrifugation at 30,000×g for 30 minutes at 4° C., the membranes were reconstituted in the original volume of standard buffer and incubated for 30 minutes at 37° C. to release bound endogenous ligands. Subsequent centrifugation and resuspension of the pellet in the initial volume of the fresh standard buffer yielded the final membrane suspension. Aliquots of 2 mL of the membrane preparations were incubated for 2 hours at 250° C. with 1 mL standard buffer containing the compound to be tested and one of the following radioligands at the final concentration indicated: [$^3$H]DAMGO, μ-selective, 0.7 nM; [$^3$H]-DPDPE, δ selective, 1.0 nM; and [$^2$H]U69563, κ-selective, 0.5 nM. The incubation was terminated by filteration through Whatman GF/B filters under vacuum at 4° C. Following two washings with 5 mL portions of ice-cold standard buffer the filters were transferred to scintillation vials and treated with 1 mL Protosol (New England Nuclear) for 30 minutes prior to addition of 0.5 mL acetic acid and 10 mL Aquasol (New England Nuclear). After shaking for 30 minutes the vials were counted at an efficiency of 40–45%. All experiments were performed in duplicates and repeated at least three times. Specific binding of each of the three radioligands was defined by performing incubations in the presence of cold DAMGO, DPDPE and U69563, respectively at a concentration of 1 mM. Values of half-maximal inhibition (IC$_{50}$) of specific binding were determined by computer assisted curve-fitting using the program LIGAND. From the measured IC$_{50}$ values, binding inhibition constants (K$_i$) were then calculated based on Cheng and Prusoffs equation. Ratios of K$_i$-values in the μ, δ, and κ binding assays are a measure of the receptor selectivity of the compounds (e.g. K$_i^\delta$/K$_i^\mu$ indicates the selectivity for μ receptors versus δ receptors).

EXAMPLE 2

In the structures of EXAMPLE 1 the reversed-turn pharmacophore with a phenol-phenyl topography similar to opioid peptides was constrained in its bioactive form by complexation with a metal ion. In Tyr-Cys-Gly-Phe-Cys-NH$_2$ (SEQ ID NO:2) the phenol moiety is unconstrained (phi, psi angles of Tyr residue) and outside the metal ion coordination sphere, while the phenyl moiety is constrained (both phi, psi angles of Phe residue) within the coordination sphere. Tyr-D-Lys-Cys-Phe presents the reverse situation: the phenyl moiety is outside the metal ion coordination sphere and the phenol moiety is constrained. Tyr-Gly-Gly-Cys-Phe-NH$_2$ (SEQ ID NO:5) presents a third situation where both the Tyr and the Phe residues are outside the metal-ion coordination sphere and are unconstrained. These three analogs demonstrate that it is possible to design conformationally constrained molecules displaying the opioid pharmacophore.

Potent δ receptor-specific metallopeptides can be obtained by optimizing the coordinates of the constrained Phenol-Phenyl moieties and aligning them with respect to the positive charge center. The positive charge center in Tyr-Cys-Gly-Phe-Cys-NH$_2$ (SEQ ID NO:2) is in the Tyr residue, while in Tyr-D-Lys-Cys-Phe it may be provided by the D-Lys side chain. It is well known that the positive charge center may be shifted away from the phenol (tyramine) moiety. A phenol-phenyl distances of about 7±1.5 Å has been proposed for the δ receptor pharmacophore. Alternate ways in which this spatial juxtaposition can be achieved on the metal-ion complexed peptide scaffold add to the structural diversity of the methods of this invention.

EXAMPLE 3

Rhenium complexed metallopeptides are synthesized on solid-phase. The linear peptides are assembled on solid-phase according to known methods of Fmoc peptide chemistry. The Cys sulfhydryl is protected as an $S^tBu$ group. After assembly of the peptide chain, including the N-terminal extensions, the $S^tBu$ group is removed by treatment with tribuylphosphine. The peptide-resin is treated with the rhenium transfer agent $ReO[V]Cl_3(PPh_3)_2$ in the presence of DBU as base and subsequently cleaved from the resin by treatment with TFA. All the peptides are purified by HPLC or other suitable means and characterized by mass spectrometry and amino acid analysis. The Re-peptides are chemically stable molecules both in solid state and in solutions. The Re-complexed metallopeptides give an unique mass spectral profile. Because of the presence of two isotopes of stable Re (Re-185 and Re-187) there is an internal signature of rhenium-complexed peptides showing two mass peaks in 1:2 ratios and differing by 2 mass units.

EXAMPLE 4

GPI and MVD assays are performed using standard procedures described in the literature. The GPI assay is considered as representative for μ receptor interactions, even though the ileum does contain κ receptors. In the MVD assay opioid effects are primarily mediated by the δ receptors, but μ and κ receptors also exist in this tissue. In both bioassays a dose-response curve with a reference compound (e.g. [D-Ala$^2$, Leu$^5$]-enkephalinamide or U50488) can be determined in each preparation. Potencies of new test compounds are determined relative to the reference compound and their $IC_{50}$ values are normalized based on an average $IC_{50}$ value obtained for the reference compound by performing several determinations with a large number of preparations. In cases where compounds might be susceptible to enzymatic degradation potencies are determined in the presence of a mixture of peptidase inhibitors (L-leucyl-leucine, 2 mM; bestatin, 10 mM; thiorphan, 0.3 mM; captopril, 10 mM). The $K_e$-values for naloxone or other antagonists is determined from the ratio of $IC_{50}$ values [DR] obtained with the compound under investigation in the presence and absence of a fixed concentration [a] of the antagonist, using the formula $K_e=[a]/[DR-1]$. New compounds that show no agonist activity are tested for possible antagonist properties against various receptor-selective opioid agonists.

The examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, and of the corresponding applications, are hereby incorporated by reference.

What is claimed is:

1. A metallopeptide comprising a manufactured peptide and pharmaceutically acceptable salts thereof comprising a metal ion-binding domain comprising two or more contiguous amino acids forming a nitrogen-containing and sulfur-containing ligand available for complexing with a metal ion and a determined biological function domain comprising a phenol moiety and a phenyl moiety and specific for one or more opioid receptors, wherein at least a portion of said biological function domain is co-extensive with at least a portion of the metal-ion binding domain, and wherein said biological-function domain is comformationally constrained upon complexing the metal-ion binding domain with a metal ion, and a metal ion complexed to the metal ion-binding domain, with the structure:

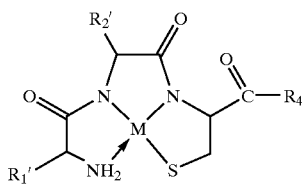

wherein
M is the metal ion;
$R_1'$ is a phenol moiety side chain;
$R_2'$ is H or a neutral or basic side chain; and
$R_4$ is an L- or D-amino acid with a phenyl moiety-containing side chain and a terminal free carboxylate or amide.

2. The metallopeptide of claim 1 wherein $R_1'$ is a side chain of an L- or D-configuration of Tyr, homoTyr, or p-hydroxy-phenylglycine, a side chain of an L- or D-configuration of an N-alkylated, N-arylated, or N-aralkylated derivative of Tyr, homoTyr, or p-hydroxy-phenylglycine, a side chain of an L- or D-configuration of Ser(O-(p-hydroxy)benzyl), Thr(O-(p-hydroxy)benzyl), Cys(S-(p-hydroxy)benzyl), Lys(N-epsilon(p-hydroxy)phenyl), or Lys(N-epsilon(p-hydroxy)benzyl).

3. The metallopeptide of claim 1 wherein the phenol hydroxyl group of $R_1'$ is para.

4. The metallopeptide of claim 1 wherein the phenol hydroxyl group of $R_1'$ is ortho or meta.

5. The metallopeptide of claim 1 wherein $R_2'$ is a side chain of an L- or D-configuration of Ala, Val, Leu, Ile, Nle, Ser, Thr, Arg, Lys, Orn, or homoArg.

6. The metallopeptide of claim 1 wherein $R_4$ comprises an L- or D-configuration of Phe, homoPhe, Phg, NaI, Trp, Dip, Bip, Ser(O-benzyl), Thr(O-benzyl), Cys(S-benzyl), or a des-carboxyl derivative of the foregoing.

7. The metallopeptide of claim 1 wherein M is an ionic form of rhenium or technetium.

8. The metallopeptide of claim 1 consisting of the peptide sequence Tyr-Gly-Cys-Phe-NH$_2$ (SEQ ID NO:3); Tyr-Ala-Cys-HPhe-NH$_2$ (SEQ ID NO:6); Tyr-Ala-Cys-Phg-NH$_2$ (SEQ ID NO:7); Tyr-Ala-Cys-Phe-NH$_2$ (SEQ ID NO:8); Tyr-Gly-Cys-Phg-NH$_2$ (SEQ ID NO:9); Tyr-Gly-Cys-HPhe-NH$_2$ (SEQ ID NO:10); Tyr-D-Lys-Cys-Phe-NH$_2$; Tyr-D-Lys-Cys-Phe; or Tyr-Val-Cys-Phe-NH$_2$ (SEQ ID NO:16), complexed to a metal ion.

9. A metallopeptide comprising a manufactured peptide and pharmaceutically acceptable salts thereof comprising a metal ion-binding domain comprising two or more contiguous amino acids forming a nitrogen-containing and sulfur-containing ligand available for complexing with a metal ion and a determined biological function domain comprising a phenol moiety and a phenyl moiety and specific for one or more opioid receptors, wherein at least a portion of said biological function domain is co-extensive with at least a portion of the metal-ion binding domain, and wherein said biological-function domain is comformationally constrained upon complexing the metal-ion binding domain with a metal ion, and a metal ion complexed to the metal ion-binding domain, with the structure:

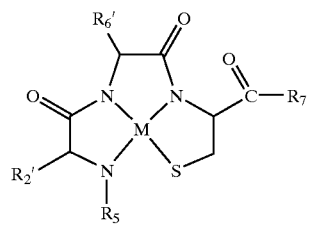

wherein
M is the metal ion;
$R_2'$ is H or a neutral or basic side chain;
$R_5$ is an L- or D-amino acid with a phenol moiety side chain, excluding des-carboxy derivatives;
$R_6'$ is H or a phenyl moiety-containing side chain, on the proviso that if $R_6'$ is H, then $R_7$ is a phenyl moiety-containing side chain; and
$R_7$ is OH, NH$_2$, a neutral or basic L- or D-amino acid with a terminal free carboxylate or amide, or a des-carboxyl derivative of a neutral or basic L- or D-amino acid.

10. The metallopeptide of claim 9 wherein $R_5$ is an L- or D-configuration of Tyr, homoTyr, or p-hydroxy-phenylglycine, an L- or D-configuration of an N-alkylated, N-arylated, or N-aralkylated derivative of Tyr, homoTyr, or p-hydroxy-phenylglycine, an L- or D-configuration of Ser(O-(p-hydroxy)benzyl), Thr(O-(p-hydroxy)benzyl), Cys(S-(p-hydroxy)benzyl), Lys(N-epsilon(p-hydroxy)phenyl), Lys(N-epsilon(p-hydroxy)benzyl), or a des-amino acid derivative of the foregoing.

11. The metallopeptide of claim 9 wherein $R_2'$ is a side chain of an L- or D-configuration of Ala, Val, Leu, Ile, Nle, Ser, Thr, Arg, Lys, Orn or homoArg.

12. The metallopeptide of claim 9 wherein $R_6'$ is a side chain of an L- or D-configuration of Phe, homoPhe, Phg, NaI, Trp, Dip, Bip, Ser(O-benzyl), Thr(O-benzyl), or Cys (S-benzyl.

13. The metallopeptide of claim 9 wherein $R_7$ comprises Gly or an L- or D-configuration of Ala, Val, Leu, Ile, Nle, Ser, Thr, Arg, Lys, Orn, homoArg, or a des-carboxyl derivative of the foregoing.

14. The metallopeptide of claim 9 wherein M is an ionic form of rhenium or technetium.

15. The metallopeptide of claim 9 consisting of the peptide sequence Tyr-Gly-Gly-Cys-Phe-NH$_2$ (SEQ ID NO:5); Tyr-Gly-D-Phe-Cys-NH$_2$; HTyr-Gly-Phe-D-Cys-NH$_2$; Tyr-Val-Phe-Cys-NH$_2$ (SEQ ID NO:15); or Tyr-Ala-Phe-Cys-OH (SEQ ID NO:18), complexed to a metal ion.

16. A metallopeptide comprising a manufactured peptide and pharmaceutically acceptable salts thereof comprising a metal ion-binding domain comprising two or more contiguous amino acids forming a nitrogen-containing and sulfur-containing ligand available for complexing with a metal ion and a determined biological function domain comprising a phenol moiety and a phenyl moiety and specific for one or more opioid receptors, wherein at least a portion of said biological function domain is co-extensive with at least a portion of the metal-ion binding domain, and wherein said biological-function domain is comformationally constrained upon complexing the metal-ion binding domain with a metal ion, and a metal ion complexed to the metal ion-binding domain, with the structure:

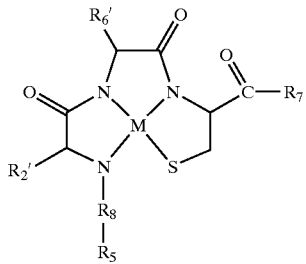

wherein

M is the metal ion;

$R_2'$ is H or a neutral or basic side chain;

$R_5$ is an L- or D-amino acid with a phenol moiety side chain, excluding des-carboxy derivatives;

$R_6'$ is a phenyl moiety-containing side chain;

$R_7$ is OH, $NH_2$, a neutral or basic L- or D-amino acid with a terminal free carboxylate or amide, or a des-carboxyl derivative of a neutral or basic L- or D-amino acid; and $R_8$ is a neutral or basic L- or D-alpha or -omega amino acid or a derivative of a neutral or basic L- or D-alpha or -omega amino acid.

17. The metallopeptide of claim 16 wherein $R_5$ is an L- or D-configuration of Tyr, homoTyr, or p-hydroxy-phenylglycine, an L- or D-configuration of an N-alkylated, N-arylated, or N-aralkylated derivative of Tyr, homoTyr, or p-hydroxy-phenylglycine, an L- or D-configuration of Ser(O-(p-hydroxy)benzyl), Thr(O-(p-hydroxy)benzyl), Cys(S-(p-hydroxy)benzyl), Lys(N-epsilon(p-hydroxy)phenyl), Lys(N-epsilon(p-hydroxy)benzyl), or a des-amino acid derivative of the foregoing.

18. The metallopeptide of claim 16 wherein $R_2'$ is a side chain of an L- or D-configuration of Ala, Val, Leu, lie, Nle, Ser, Thr, Arg, Lys, Orn, or homoArg.

19. The metallopeptide of claim 16 wherein $R_6'$ is a side chain of an L- or D-configuration of Phe, homoPhe, Phg, NaI, Trp, Dip, Bip, Ser(O-benzyl), Thr(O-benzyl), or Cys (S-benzyl).

20. The metallopeptide of claim 16 wherein $R_7$ comprises Gly or an L- or D-configuration of Ala, Val, Leu, lie, Nle, Ser, Thr, Arg, Lys, Orn or homoArg, or a des-carboxyl derivative of the foregoing.

21. The metallopeptide of claim 16 wherein $R_8$ is Gly or an L- or D-configuration of Ala, Val, Leu, lie, Nle, Phe, Lys, Cys, Orn, Abu, Dpr, or a di-basic amino acid incorporated through an alpha or omega amino group, β-Ala.

22. The metallopeptide of claim 16 wherein M is an ionic form of rhenium or technetium.

23. The metallopeptide of claim 16 consisting of the peptide sequence Tyr-Ala-Gly-Phe-Cys-$NH_2$ (SEQ ID NO:4); Tyr-Cys-Gly-Phe-Cys-$NH_2$ (SEQ ID NO:2); Tyr-β-Ala-Gly-Phe-Cys-$NH_2$ (SEQ ID NO:11); Tyr-p-Ala-Gly-Phe-D-Cys-$NH_2$; HTyr-p-Ala-Gly-Phe-Cys-$NH_2$ (SEQ ID NO:12); HTyr-β-Ala-Gly-Phe-D-Cys-$NH_2$; or Tyr-[NH($CH_2$)$_3$—CH($NH_2$)—CO]-Gly-Phe-D-Cys-$NH_2$, complexed to a metal ion.

24. A metallopeptide comprising a manufactured peptide and pharmaceutically acceptable salts thereof comprising a metal ion-binding domain comprising two or more contiguous amino acids forming a nitrogen-containing and sulfur-containing ligand available for complexing with a metal ion and a determined biological function domain comprising a phenol moiety and a phenyl moiety and specific for one or more opioid receptors, wherein at least a portion of said biological function domain is co-extensive with at least a portion of the metal-ion binding domain, and wherein said biological-function domain is comformationally constrained upon complexing the metal-ion binding domain with a metal ion, and a metal ion complexed to the metal ion-binding domain, with the structure

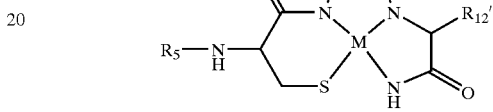

wherein

M is the metal ion;

$R_5$ is an L- or D-amino acid with a phenol moiety side chain, excluding des-carboxy derivatives;

$R_6'$ is a phenyl moiety-containing side chain; and $R_{12}'$ is a neutral side chain.

25. The metallopeptide of claim 24 wherein $R_5$ is an L- or D-configuration of Tyr, homoTyr, or p-hydroxy-phenylglycine, an L- or D-configuration of an N-alkylated, N-arylated, or N-aralkylated derivative of Tyr, homoTyr, or p-hydroxy-phenylglycine, an L- or D-configuration of Ser(O-(p-hydroxy)benzyl), Thr(O-(p-hydroxy)benzyl), Cys(S-(p-hydroxy)benzyl), Lys(N-epsilon(p-hydroxy)phenyl), or Lys (N-epsilon(p-hydroxy)benzyl), or a des-amino acid derivative of the foregoing.

26. The metallopeptide of claim 24 wherein $R_6'$ is a side chain of an L- or D-configuration of Phe, homoPhe, Phg, NaI, Trp, Dip, Bip, Ser(O-benzyl), Thr(O-benzyl), or Cys (S-benzyl).

27. The metallopeptide of claim 24 wherein $R_{12}'$ is H or a side chain of an L- or D-configuration of Ala, Val, Leu, lie, Nle, or Phe.

28. The metallopeptide of claim 24 wherein M is an ionic form of rhenium or technetium.

29. The metallopeptide of claim 24 consisting of the peptide sequence Tyr-Cys-D-Phe-Gly-$NH_2$ complexed to a metal ion.

30. A metallopeptide comprising a manufactured peptide and pharmaceutically acceptable salts thereof comprising a metal ion-binding domain comprising two or more contiguous amino acids forming a nitrogen-containing and sulfur-containing ligand available for complexing with a metal ion and a determined biological function domain comprising a phenol moiety and a phenyl moiety and specific for one or more opioid receptors, wherein at least a portion of said biological function domain is co-extensive with at least a portion of the metal-ion binding domain, and wherein said biological-function domain is comformationally constrained upon complexing the metal-ion binding domain with a metal ion, and a metal ion complexed to the metal ion-binding domain, with the structure

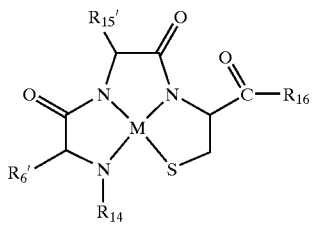

wherein

M is the metal ion; and $R_6'$ is a phenyl moiety-containing side chain;

$R_{14}$ is a neutral or basic L- or D-alpha or -omega amino acid, or a derivative thereof;

$R_{15}'$ is a side chain comprising hydrogen bond forming groups; and $R_{16}$ an L- or D-amino acid with a phenol moiety side chain and a terminal free carboxylate or amide.

31. The metallopeptide of claim 30 wherein $R_6'$ is a side chain of an L- or D-configuration of Phe, homoPhe, Phg, NaI, Trp, Dip, Bip, Ser(O-benzyl), Thr(O-benzyl), or Cys (S-benzyl).

32. The metallopeptide of claim 30 wherein $R_{14}$ is Gly or an L- or D-configuration of Ala, Val, Leu, lie, Nle, Phe, Trp, Lys, Orn, Abu, Dpr, a di-basic amino acid, β-Ala, or a higher omega amino acid with a free amino group.

33. The metallopeptide of claim 30 wherein $R_{15}'$ is a side chain of an L- or D-configuration of Ser, Thr, Asp, Glu, Lys, Orn, Arg, or homoArg.

34. The metallopeptide of claim 30 wherein $R_{16}$ comprises an L- or D-configuration of Tyr, homoTyr, p-hydroxyphenylglycine, Ser(O-(p-hydroxy)benzyl), Thr(O-(p-hydroxy)benzyl), Cys(O-(p-hydroxy)benzyl), Lys(N-epsilon (p-hydroxy)phenyl), Lys(N-epsilon(p-hydroxy)benzyl), a des-carboxy derivative of the foregoing, or an amide derivative of the foregoing.

35. The metallopeptide of claim 30 wherein M is an ionic form of rhenium or technetium.

36. The metallopeptide of claim 30 consisting of the peptide sequence $NH_2(CH_2)_4$—CO—HPhe-Asp-Cys-HTyr-$NH_2$ (SEQ ID NO:14) or $NH_2(CH_2)_4$—CO-Phe-Asp-Cys-HTyr-$NH_2$ (SEQ ID NO:13), complexed to a metal ion.

* * * * *

SEQUENCE LISTING

<160> NUMBER OF SEQ ID NOS: 20

<210> SEQ ID NO 1
<211> LENGTH: 4
<212> TYPE: PRT
<213> ORGANISM: Artificial Sequence
<220> FEATURE:
<223> OTHER INFORMATION: metal binding sequence

<400> SEQUENCE: 1

Gly Gly Gly Gly
1

<210> SEQ ID NO 2
<211> LENGTH: 5
<212> TYPE: PRT
<213> ORGANISM: Artificial Sequence
<220> FEATURE:
<223> OTHER INFORMATION: opioid receptor specific metallopeptide
      sequence

<400> SEQUENCE: 2

Tyr Cys Gly Phe Cys
1               5

<210> SEQ ID NO 3
<211> LENGTH: 4
<212> TYPE: PRT
<213> ORGANISM: Artificial Sequence

```
<220> FEATURE:
<223> OTHER INFORMATION: opioid receptor specific metallopeptide
      sequence

<400> SEQUENCE: 3

Tyr Gly Cys Phe
1

<210> SEQ ID NO 4
<211> LENGTH: 5
<212> TYPE: PRT
<213> ORGANISM: Artificial Sequence
<220> FEATURE:
<223> OTHER INFORMATION: opioid receptor specific metallopeptide
      sequence

<400> SEQUENCE: 4

Tyr Ala Gly Phe Cys
1               5

<210> SEQ ID NO 5
<211> LENGTH: 5
<212> TYPE: PRT
<213> ORGANISM: Artificial Sequence
<220> FEATURE:
<223> OTHER INFORMATION: opioid receptor specific metallopeptide
      sequence

<400> SEQUENCE: 5

Tyr Gly Gly Cys Phe
1               5

<210> SEQ ID NO 6
<211> LENGTH: 4
<212> TYPE: PRT
<213> ORGANISM: Artificial Sequence
<220> FEATURE:
<223> OTHER INFORMATION: opioid receptor specific metallopeptide
      sequence
<220> FEATURE:
<221> NAME/KEY: MISC_FEATURE
<222> LOCATION: (4)..(4)
<223> OTHER INFORMATION: HPhe

<400> SEQUENCE: 6

Tyr Ala Cys Xaa
1

<210> SEQ ID NO 7
<211> LENGTH: 4
<212> TYPE: PRT
<213> ORGANISM: Artificial Sequence
<220> FEATURE:
<223> OTHER INFORMATION: opioid receptor specific metallopeptide
      sequence
<220> FEATURE:
<221> NAME/KEY: MISC_FEATURE
<222> LOCATION: (4)..(4)
<223> OTHER INFORMATION: Phg

<400> SEQUENCE: 7

Tyr Ala Cys Xaa
1

<210> SEQ ID NO 8
<211> LENGTH: 4
<212> TYPE: PRT
<213> ORGANISM: Artificial Sequence
```

```
<220> FEATURE:
<223> OTHER INFORMATION: opioid receptor specific metallopeptide
      sequence

<400> SEQUENCE: 8

Tyr Ala Cys Phe
1

<210> SEQ ID NO 9
<211> LENGTH: 4
<212> TYPE: PRT
<213> ORGANISM: Artificial Sequence
<220> FEATURE:
<223> OTHER INFORMATION: opioid receptor specific metallopeptide
      sequence
<220> FEATURE:
<221> NAME/KEY: MISC_FEATURE
<222> LOCATION: (4)..(4)
<223> OTHER INFORMATION: Phg

<400> SEQUENCE: 9

Tyr Gly Cys Xaa
1

<210> SEQ ID NO 10
<211> LENGTH: 4
<212> TYPE: PRT
<213> ORGANISM: Artificial Sequence
<220> FEATURE:
<223> OTHER INFORMATION: opioid receptor specific metallopeptide
      sequence
<220> FEATURE:
<221> NAME/KEY: MISC_FEATURE
<222> LOCATION: (4)..(4)
<223> OTHER INFORMATION: HPhe

<400> SEQUENCE: 10

Tyr Gly Cys Xaa
1

<210> SEQ ID NO 11
<211> LENGTH: 5
<212> TYPE: PRT
<213> ORGANISM: Artificial Sequence
<220> FEATURE:
<223> OTHER INFORMATION: opioid receptor specific metallopeptide
      sequence
<220> FEATURE:
<221> NAME/KEY: MISC_FEATURE
<222> LOCATION: (2)..(2)
<223> OTHER INFORMATION: BAla

<400> SEQUENCE: 11

Tyr Xaa Gly Phe Cys
1               5

<210> SEQ ID NO 12
<211> LENGTH: 5
<212> TYPE: PRT
<213> ORGANISM: Artificial Sequence
<220> FEATURE:
<223> OTHER INFORMATION: opioid receptor specific metallopeptide
      sequence
<220> FEATURE:
<221> NAME/KEY: MISC_FEATURE
<222> LOCATION: (1)..(1)
<223> OTHER INFORMATION: HTyr
<220> FEATURE:
<221> NAME/KEY: MISC_FEATURE
<222> LOCATION: (2)..(2)
<223> OTHER INFORMATION: BAla
```

```
<400> SEQUENCE: 12

Xaa Xaa Gly Phe Cys
1               5

<210> SEQ ID NO 13
<211> LENGTH: 5
<212> TYPE: PRT
<213> ORGANISM: Artificial Sequence
<220> FEATURE:
<223> OTHER INFORMATION: opioid receptor specific metallopeptide
      sequence
<220> FEATURE:
<221> NAME/KEY: MISC_FEATURE
<222> LOCATION: (1)..(1)
<223> OTHER INFORMATION: NH2(CH2)4-CO
<220> FEATURE:
<221> NAME/KEY: MISC_FEATURE
<222> LOCATION: (5)..(5)
<223> OTHER INFORMATION: HTyr

<400> SEQUENCE: 13

Xaa Phe Asp Cys Xaa
1               5

<210> SEQ ID NO 14
<211> LENGTH: 5
<212> TYPE: PRT
<213> ORGANISM: Artificial Sequence
<220> FEATURE:
<223> OTHER INFORMATION: opioid receptor specific metallopeptide
      sequence
<220> FEATURE:
<221> NAME/KEY: MISC_FEATURE
<222> LOCATION: (1)..(1)
<223> OTHER INFORMATION: NH2(CH2)4-CO
<220> FEATURE:
<221> NAME/KEY: MISC_FEATURE
<222> LOCATION: (2)..(2)
<223> OTHER INFORMATION: HPhe
<220> FEATURE:
<221> NAME/KEY: MISC_FEATURE
<222> LOCATION: (5)..(5)
<223> OTHER INFORMATION: HTyr

<400> SEQUENCE: 14

Xaa Xaa Asp Cys Xaa
1               5

<210> SEQ ID NO 15
<211> LENGTH: 4
<212> TYPE: PRT
<213> ORGANISM: Artificial Sequence
<220> FEATURE:
<223> OTHER INFORMATION: opioid receptor specific metallopeptide
      sequence

<400> SEQUENCE: 15

Thr Val Phe Cys
1

<210> SEQ ID NO 16
<211> LENGTH: 4
<212> TYPE: PRT
<213> ORGANISM: Artificial Sequence
```

```
<220> FEATURE:
<223> OTHER INFORMATION: opioid receptor specific metallopeptide
      sequence

<400> SEQUENCE: 16

Tyr Val Cys Phe
1

<210> SEQ ID NO 17
<211> LENGTH: 4
<212> TYPE: PRT
<213> ORGANISM: Artificial Sequence
<220> FEATURE:
<223> OTHER INFORMATION: opioid receptor specific metallopeptide
      sequence

<400> SEQUENCE: 17

Phe Tyr Lys Cys
1

<210> SEQ ID NO 18
<211> LENGTH: 4
<212> TYPE: PRT
<213> ORGANISM: Artificial Sequence
<220> FEATURE:
<223> OTHER INFORMATION: opioid receptor specific metallopeptide
      sequence

<400> SEQUENCE: 18

Tyr Ala Phe Cys
1

<210> SEQ ID NO 19
<211> LENGTH: 4
<212> TYPE: PRT
<213> ORGANISM: Artificial Sequence
<220> FEATURE:
<223> OTHER INFORMATION: opioid receptor specific metallopeptide
      sequence

<400> SEQUENCE: 19

Tyr Cys Gly Cys
1

<210> SEQ ID NO 20
<211> LENGTH: 5
<212> TYPE: PRT
<213> ORGANISM: Artificial Sequence
<220> FEATURE:
<223> OTHER INFORMATION: opioid receptor specific metallopeptide
      sequence
<220> FEATURE:
<221> NAME/KEY: MISC_FEATURE
<222> LOCATION: (2)..(2)
<223> OTHER INFORMATION: BAla

<400> SEQUENCE: 20

Tyr Xaa Phe Gly Cys
1               5
```